(12) United States Patent
Tsunoda et al.

(10) Patent No.: US 8,541,546 B2
(45) Date of Patent: Sep. 24, 2013

(54) WDRPUH EPITOPE PEPTIDES AND VACCINES CONTAINING THE SAME

(75) Inventors: Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/132,891

(22) PCT Filed: Dec. 3, 2009

(86) PCT No.: PCT/JP2009/006573
§ 371 (c)(1),
(2), (4) Date: Aug. 17, 2011

(87) PCT Pub. No.: WO2010/064430
PCT Pub. Date: Jun. 10, 2010

(65) Prior Publication Data
US 2011/0293645 A1    Dec. 1, 2011

Related U.S. Application Data

(60) Provisional application No. 61/200,962, filed on Dec. 5, 2008, provisional application No. 61/209,704, filed on Mar. 9, 2009.

(51) Int. Cl.
*C07K 4/12* (2006.01)
*A61K 38/04* (2006.01)

(52) U.S. Cl.
USPC .......................................... 530/326; 514/885

(58) Field of Classification Search
None
See application file for complete search history.

(56) References Cited

U.S. PATENT DOCUMENTS

| | | |
|---|---|---|
| 7,425,612 B2 | 9/2008 | Nakamura et al. |
| 7,705,141 B2 | 4/2010 | Nakamura et al. |
| 7,847,065 B2 | 12/2010 | Nakamura et al. |
| 2006/0019252 A1 | 1/2006 | Nakamura et al. |
| 2008/0207549 A1 | 8/2008 | Nakamura et al. |
| 2010/0291567 A1 | 11/2010 | Nakamura et al. |

FOREIGN PATENT DOCUMENTS

| | | |
|---|---|---|
| WO | WO 03/104276 A2 | 12/2003 |
| WO | WO 2004/024766 A1 | 3/2004 |
| WO | WO 2008/126413 A1 | 10/2008 |

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990) pp. 126-128 and 228-234.*
Silva, et al., "Identification of a novel molecular target gene, *WDRPUH*, abundantly expressed in human hepatocellular carcinoma," *Proceedings 62th Annual Meeting of the Japanese Cancer Association*, #3327-OP, p. 284 (2003).
Silva, et al., "Identification of *WDRPUH*, a novel gene abundantly expressed in human hepatocellular carcinomas as a molecular target for diagnosis and treatment," *Proceedings of the American Association for Cancer Research*, vol. 45, #1717, p. 395 (Mar. 2004).
Adams, et al. EMBL Accession No. AQ045454, 1 page. (Jul. 14, 2001).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Bjorn, et al., "*PRP4 (RNA4)* from *Saccharomyces cerevisiae*: Its Gene Product Is Associated with the U4/U6 Small Nuclear Ribonucleoprotein Particle," *Mol Cell Biol.*, vol. 9(9), pp. 3698-3709 (Sep. 1989).
Boon, "Tumor Antigens Recognized by Cytolytic T Lymphocytes: Present Perspectives for Specific Immunotherapy," *Int. J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al., "Cytolytic T-cell responses of cancer patients vaccinated with a MAGE antigen," *Immunol Rev.*, vol. 188, pp. 33-42 (Oct. 2002).
Feldman, et al., "A Complex of Cdc4p, Skp1p, and Cdc53p/Cullin Catalyzes Ubiquitination of the Phosphorylated CDK Inhibitor Sic1p," *Cell*, vol. 91(2), pp. 221-230 (Oct. 17, 1997).
Fujie, et al., "A *MAGE-1*-Encoded HLA-A24-Binding Synthetic Peptide Induces Specific Anti-Tumor Cytotoxic T Lymphocytes," *Int J Cancer.*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Nolte, et al., "Expression of proliferation associated antigens and detection of numerical chromosome aberrations in primary human liver tumours: relevance to tumour characteristics and prognosis," *J Clin Pathol.*, vol. 51(1), pp. 47-51 (Jan. 1998).
Oiso, et al., "A Newly Identified *MAGE-3*-Derived Epitope Recognized by HLA-A24-Restricted Cytotoxic T Lymphocytes," *Int J Cancer*, vol. 81(3), pp. 387-394 (May 5, 1999).
Pryer, et al., "Cytosolic Sec13p Complex Is Required for Vesicle Formation from the Endoplasmic Reticulum in Vitro," *J Cell Biol.*, vol. 120(4), pp. 865-875 (Feb. 1993).

(Continued)

*Primary Examiner* — Prema Mertz
(74) *Attorney, Agent, or Firm* — Kilpatrick Townsend & Stockton LLP

(57) ABSTRACT

The present invention provides peptides containing the amino acid sequence of SEQ ID NOs: 1, 2, 3, 4, 16, 17, 30, 31, 34, 36, 37, 40, 41, 45, 49, 55, 57 and 61, as well as peptides containing the above-mentioned amino acid sequences in which 1, 2, or several amino acid(s) are substituted, deleted, inserted or added, but still have cytotoxic T cell inducibility. The present invention also provides drugs for treating or preventing tumors, which drugs containing these peptides. The peptides of the present invention can also be used as vaccines.

6 Claims, 6 Drawing Sheets

(56) References Cited

OTHER PUBLICATIONS

Rosenberg, et al, "Cancer Immunotherapy: moving beyond current vaccines," *Nat Med.*, vol. 10(9), pp. 909-915 (Sep. 2004).

Silva, et al., "Identification of a novel molecular target gene, *WDRPUH*, abundantly expressed in human hepatocellular carcinoma," *Proceedings 62th Annual Meeting of the Japanese Cancer Association*, #3327-0P, p. 284 (2003).

Silva, et al., "Identification of *WDRPUH*, a novel gene abundantly expressed in human hepatocellular carcinomas as a molecular target for diagnosis and treatment," *Proceedings of the American Association for Cancer Research*, vol. 45, #1717, p. 395 (2004).

Silva, et al., "WDRPUH, a novel WD-repeat protein highly expressed in hepatocellular carcinoma, is involved in proliferation of cancer cells," *Proceedings of the American Association for Cancer Research*, vol. 46, #2337, pp. 548-549 (Apr. 2005).

Silva, et al., "WDRPUH, A Novel WD-Repeat-Containing Protein, Is Highly Expressed in Human Hepatocellular Carcinoma and Involved in Cell Proliferation," *Neoplasia*, vol. 7(4), pp. 348-355 (Apr. 2005).

Strausberg, et al., EMBL Accession No. BC025392, 3 pages. (Mar. 12, 2002).

Sugano, et al., EMBL Accession AK074435, 2 pages. (Feb. 15, 2002).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Vaisman, et al. "The role of *Saccharomyces cerevisiae* Cdc40p in DNA replication and mitotic spindle formation and/or maintenance," *Mol Gen Genet.*, vol. 247(2), pp. 123-136 (Apr. 20, 1995).

Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

U.S. Appl. No. 12/910,015, filed Oct. 22, 2010, 142 pages.

EMBL Accession No. BE348232, 2 pages. (Jul. 21, 2000).

Dionne, Sara O., et al., "Her-2/neu altered peptide ligand-induced CTL responses: implications for peptides with increased HLA affinity and T-cell-receptor interaction," *Cancer Immunol Immunother*, 2004, 53:307-314.

Hoffmann, Thomas K., et al., "The Ability of Variant Peptides to Reverse the Nonresponsiveness of T Lymphocytes to the Wild-Type Sequence p53$_{264-272}$ Epitope," *J. Immunology*, 2002, 168:1338-1347.

Kondo, A., et al., "Prominent Roles of Secondary Anchor Residues in Peptide Binding to HLA-A24 Human Class I Molecules," *J. Immunology*, 1995, 155:4307-4312.

Kubo, Ralph T., et al., "Definition of Specific Peptide Motifs for Four Major HLA-A Alleles," *J. Immunology*, 1994, 152:3913-3924.

Rammensee, Hans-Georg, et al., "MHC ligands and peptide motifs: first listing," *Immunogenetics*, 1995, 41:178-228.

Zaremba, Sam, et al., "Identification of an Enhancer Agonist Cytotoxic T Lymphocyte Peptide from Human Carcinoembryonic Antigen," *Cancer Research*, Oct. 15, 1997, 57:4570-4577.

Adams, et al., *J Immunol Methods*, vol. 185(2), pp. 181-190 (Sep. 25, 1995).

Dionne, et al., *Cancer Immunol Immunother*, vol. 52(4), pp. 199-206 (Apr. 2003, Epub Feb. 18, 2003).

Falk, et al., *Nature*, vol. 351(6324), pp. 290-296 (May 23, 1991).

Parker, et al., *J Immunol*, vol. 152(1), pp. 163-175 (Jan. 1, 1994).

Schueler-Furman, et al., *Protein Sci*, vol. 9(9), pp. 1838-1846 (Sep. 2000).

Stevanovic, et al., *Nat Rev Cancer*, vol. 2(7), pp. 514-520 (Jul. 2002).

GenBank Accession No. NM_145054, "*Homo sapiens* WD repeat domain 16 (WDR16), transcript variant 2, mRNA," 3 pgs. (Feb. 28, 2007).

\* cited by examiner

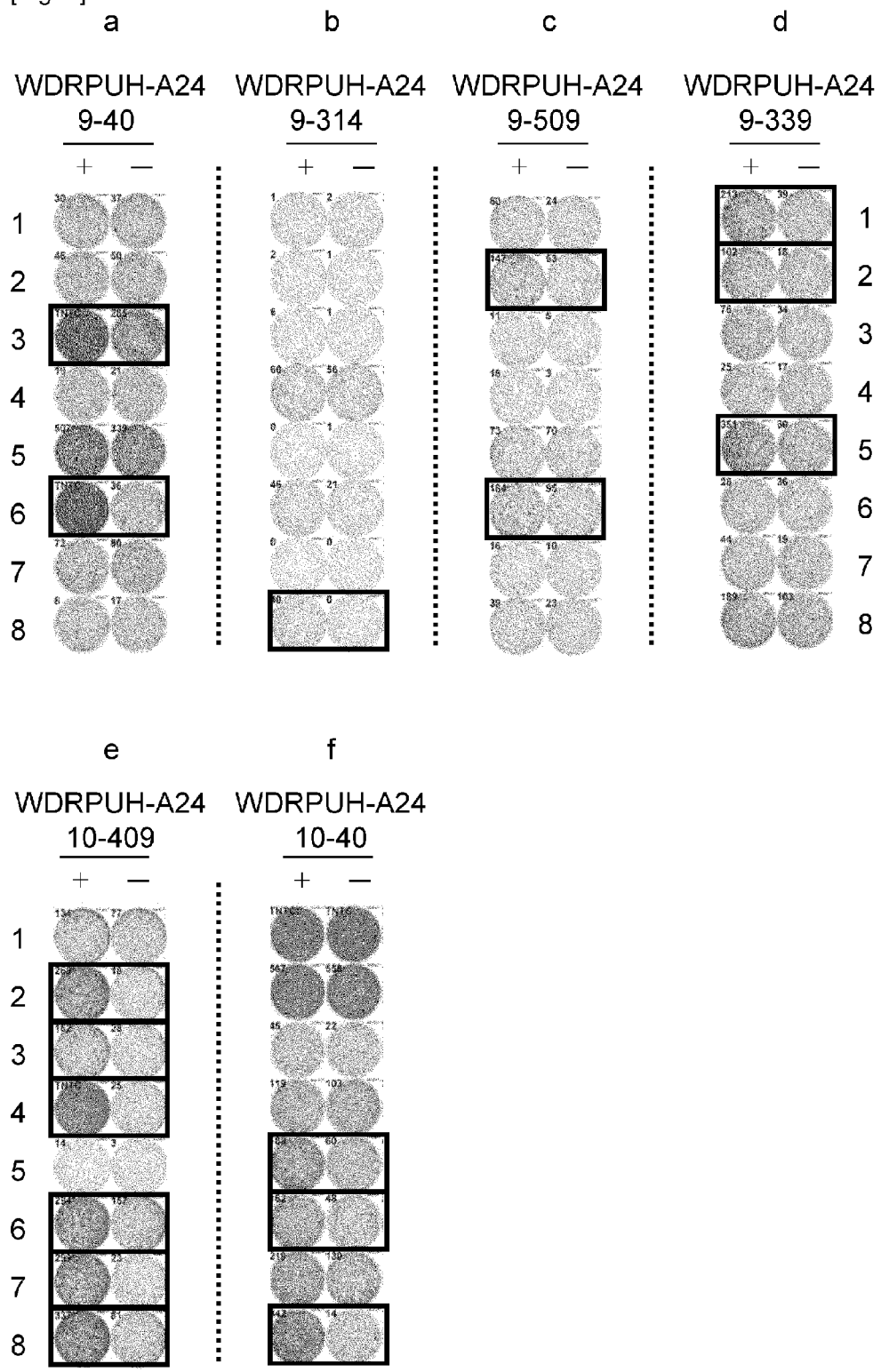

[Fig. 2]
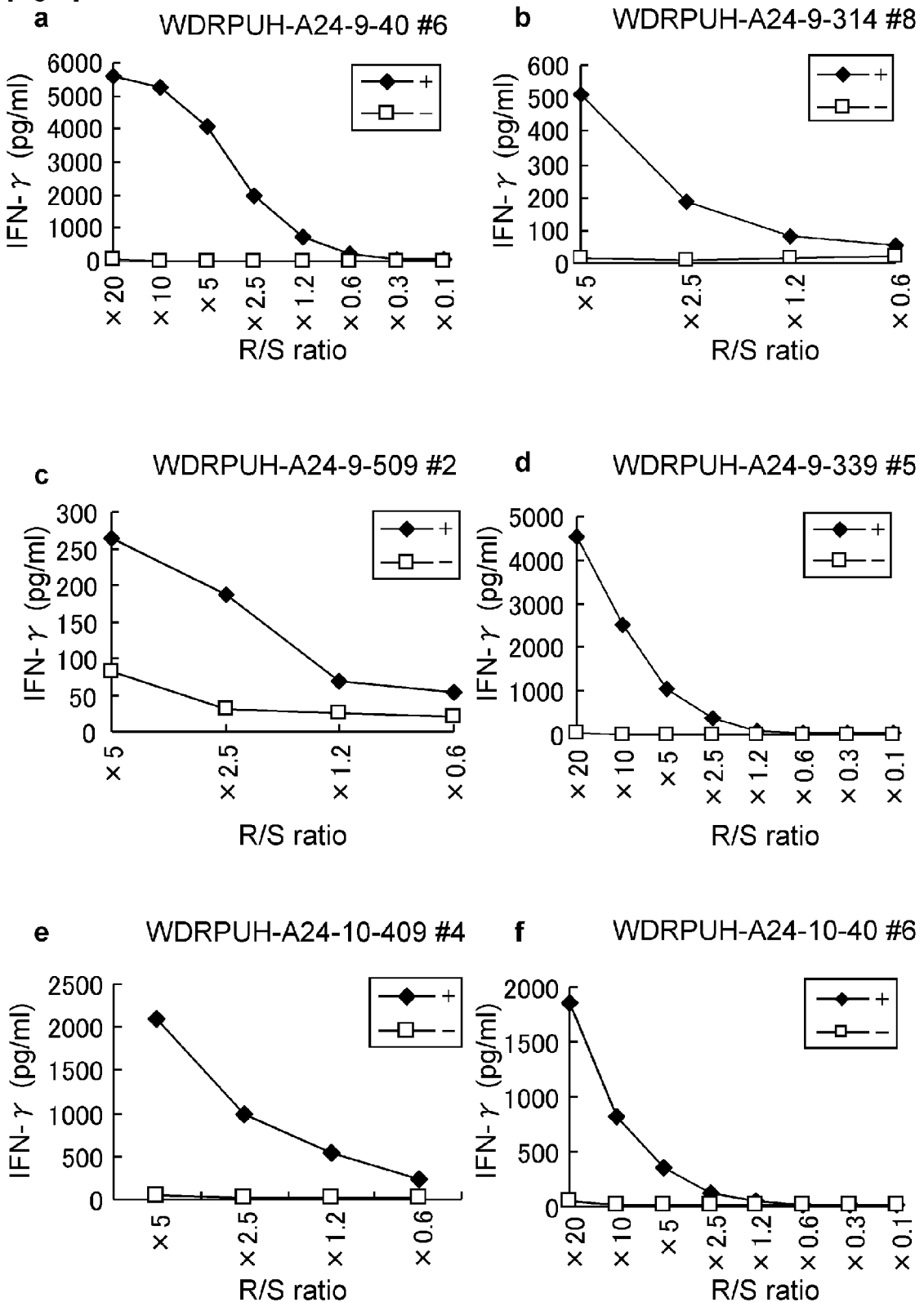

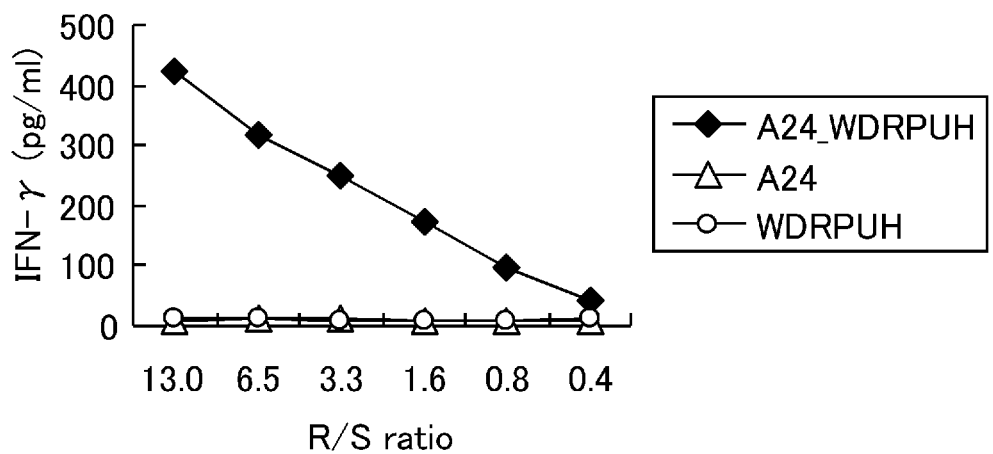
[Fig. 3]

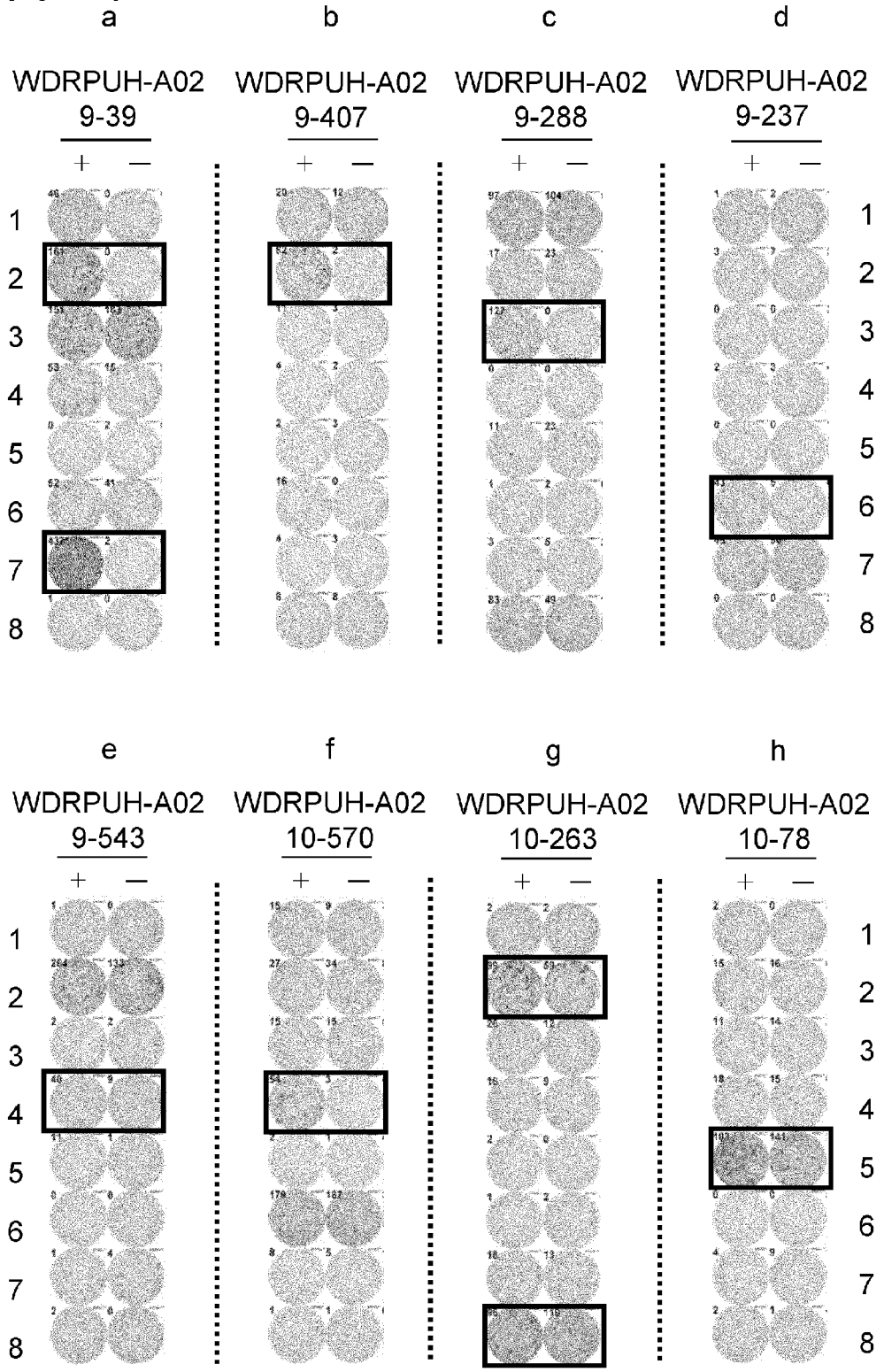

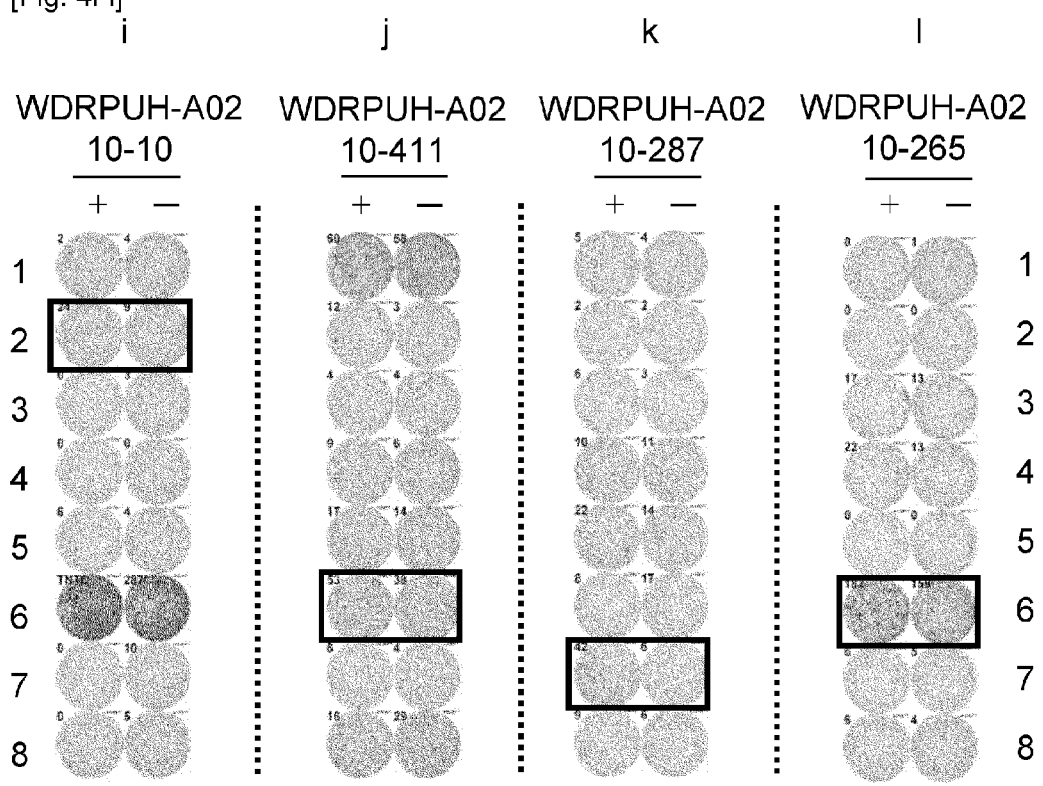

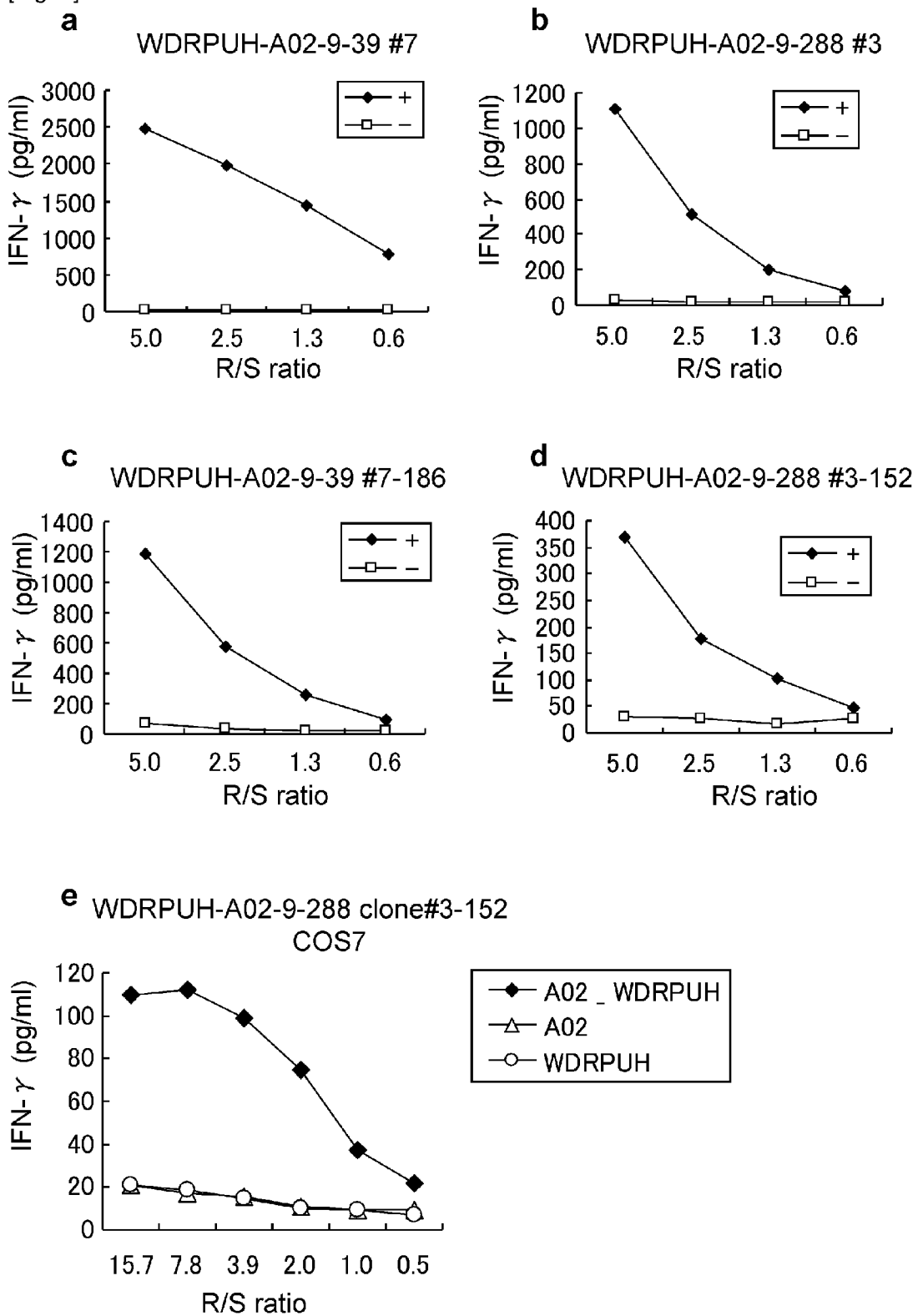
[Fig. 5]

SEQUENCE LISTING

```
<160> NUMBER OF SEQ ID NOS: 68

<210> SEQ ID NO 1
<211> LENGTH: 9
<212> TYPE: PRT
<213> ORGANISM: Artificial
<220> FEATURE:
<223> OTHER INFORMATION: An artificially synthesized peptide

<400> SEQUENCE: 1

Ile Tyr Pro Leu Gly Cys Thr Val Leu
1               5

<210> SEQ ID NO 2
<211> LENGTH: 9
<212> TYPE: PRT
<213> ORGANISM: Artificial
<220> FEATURE:
<223> OTHER INFORMATION: an artificially synthesized peptide

<400> SEQUENCE: 2

Ile Tyr Arg Val Ser Phe Thr Asp Phe
1               5

<210> SEQ ID NO 3
<211> LENGTH: 9
<212> TYPE: PRT
<213> ORGANISM: Artificial
<220> FEATURE:
<223> OTHER INFORMATION: an artificially synthesized peptide

<400> SEQUENCE: 3

Cys Tyr His Pro Glu Glu Phe Gln Ile
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized peptide

<400> SEQUENCE: 4

Val Phe Pro Phe Gly Thr Ala Glu Leu
1               5
```

```
<210> SEQ ID NO 5
<211> LENGTH: 9
<212> TYPE: PRT
<213> ORGANISM: Artificial
<220> FEATURE:
<223> OTHER INFORMATION: an artificially synthesized peptide

<400> SEQUENCE: 5

Ser Phe Thr Asp Phe Lys Glu Thr Leu
1               5

<210> SEQ ID NO 6
<211> LENGTH: 9
<212> TYPE: PRT
<213> ORGANISM: Artificial
<220> FEATURE:
<223> OTHER INFORMATION: an artificially synthesized peptide

<400> SEQUENCE: 6

Ala Phe Ala Pro Glu Thr Gly Arg Leu
1               5

<210> SEQ ID NO 7
<211> LENGTH: 9
<212> TYPE: PRT
<213> ORGANISM: Artificial
<220> FEATURE:
<223> OTHER INFORMATION: an artificially synthesized peptide

<400> SEQUENCE: 7

Ala Phe Ser Pro Asn Asp Leu Tyr Leu
1               5

<210> SEQ ID NO 8
<211> LENGTH: 9
<212> TYPE: PRT
<213> ORGANISM: Artificial
<220> FEATURE:
<223> OTHER INFORMATION: an artificially synthesized peptide

<400> SEQUENCE: 8

Lys Met Asn Pro Arg Thr Lys Leu Leu
1               5

<210> SEQ ID NO 9
<211> LENGTH: 9
<212> TYPE: PRT
<213> ORGANISM: Artificial
<220> FEATURE:
<223> OTHER INFORMATION: an artificially synthesized peptide

<400> SEQUENCE: 9

Arg Cys Leu Lys Met Gly Gly Leu Leu
1               5

<210> SEQ ID NO 10
<211> LENGTH: 9
<212> TYPE: PRT
<213> ORGANISM: Artificial
<220> FEATURE:
<223> OTHER INFORMATION: an artificially synthesized peptide

<400> SEQUENCE: 10

Lys Asn Arg Glu Leu Leu Ala Arg Leu
1               5

<210> SEQ ID NO 11
<211> LENGTH: 9
```

```
<212> TYPE: PRT
<213> ORGANISM: Artificial
<220> FEATURE:
<223> OTHER INFORMATION: an artificially synthesized peptide

<400> SEQUENCE: 11

Ala Tyr Trp Glu Val Phe Asp Gly Thr
1               5

<210> SEQ ID NO 12
<211> LENGTH: 9
<212> TYPE: PRT
<213> ORGANISM: Artificial
<220> FEATURE:
<223> OTHER INFORMATION: an artificially synthesized peptide

<400> SEQUENCE: 12

Lys Phe Ser Leu Gly Val Ser Ala Ile
1               5

<210> SEQ ID NO 13
<211> LENGTH: 10
<212> TYPE: PRT
<213> ORGANISM: Artificial
<220> FEATURE:
<223> OTHER INFORMATION: an artificially synthesized peptide

<400> SEQUENCE: 13

Gly Tyr Lys Pro Ile Lys Lys Ile Gln Leu
1               5                   10

<210> SEQ ID NO 14
<211> LENGTH: 10
<212> TYPE: PRT
<213> ORGANISM: Artificial
<220> FEATURE:
<223> OTHER INFORMATION: an artificially synthesized peptide

<400> SEQUENCE: 14

Glu Tyr Ile Ala Ser Gly Gln Val Thr Phe
1               5                   10

<210> SEQ ID NO 15
<211> LENGTH: 10
<212> TYPE: PRT
<213> ORGANISM: Artificial
<220> FEATURE:
<223> OTHER INFORMATION: an artificially synthesized peptide

<400> SEQUENCE: 15

Cys Tyr His Pro Glu Glu Phe Gln Ile Ile
1               5                   10

<210> SEQ ID NO 16
<211> LENGTH: 10
<212> TYPE: PRT
<213> ORGANISM: Artificial
<220> FEATURE:
<223> OTHER INFORMATION: an artificially synthesized peptide

<400> SEQUENCE: 16

Met Tyr Val Ile Asn Asn Ala His Arg Ile
1               5                   10

<210> SEQ ID NO 17
<211> LENGTH: 10
<212> TYPE: PRT
<213> ORGANISM: Artificial
```

```
<220> FEATURE:
<223> OTHER INFORMATION: an artificially synthesized peptide

<400> SEQUENCE: 17

Ile Tyr Pro Leu Gly Cys Thr Val Leu Ile
1               5                   10

<210> SEQ ID NO 18
<211> LENGTH: 10
<212> TYPE: PRT
<213> ORGANISM: Artificial
<220> FEATURE:
<223> OTHER INFORMATION: an artificially synthesized peptide

<400> SEQUENCE: 18

Phe Tyr Leu Gly Thr Thr Thr Gly Asp Ile
1               5                   10

<210> SEQ ID NO 19
<211> LENGTH: 10
<212> TYPE: PRT
<213> ORGANISM: Artificial
<220> FEATURE:
<223> OTHER INFORMATION: an artificially synthesized peptide

<400> SEQUENCE: 19

Gly Phe Asn Gly His Val Pro Thr Gly Leu
1               5                   10

<210> SEQ ID NO 20
<211> LENGTH: 10
<212> TYPE: PRT
<213> ORGANISM: Artificial
<220> FEATURE:
<223> OTHER INFORMATION: an artificially synthesized peptide

<400> SEQUENCE: 20

Val Phe Asp Gly Thr Val Ile Arg Glu Leu
1               5                   10

<210> SEQ ID NO 21
<211> LENGTH: 10
<212> TYPE: PRT
<213> ORGANISM: Artificial
<220> FEATURE:
<223> OTHER INFORMATION: an artificially synthesized peptide

<400> SEQUENCE: 21

His Phe Val Thr Gly Gly Asn Asp His Leu
1               5                   10

<210> SEQ ID NO 22
<211> LENGTH: 10
<212> TYPE: PRT
<213> ORGANISM: Artificial
<220> FEATURE:
<223> OTHER INFORMATION: an artificially synthesized peptide

<400> SEQUENCE: 22

Arg Asn Gln Met Ile Leu Ala Asn Thr Leu
1               5                   10

<210> SEQ ID NO 23
<211> LENGTH: 10
<212> TYPE: PRT
<213> ORGANISM: Artificial
<220> FEATURE:
<223> OTHER INFORMATION: an artificially synthesized peptide
```

```
<400> SEQUENCE: 23

Val Phe Pro Phe Gly Thr Ala Glu Leu Phe
1               5                   10

<210> SEQ ID NO 24
<211> LENGTH: 10
<212> TYPE: PRT
<213> ORGANISM: Artificial
<220> FEATURE:
<223> OTHER INFORMATION: an artificially synthesized peptide

<400> SEQUENCE: 24

Ile Phe Ser Arg Cys Arg Asp Glu Met Phe
1               5                   10

<210> SEQ ID NO 25
<211> LENGTH: 10
<212> TYPE: PRT
<213> ORGANISM: Artificial
<220> FEATURE:
<223> OTHER INFORMATION: an artificially synthesized peptide

<400> SEQUENCE: 25

His Phe Asp Ala Val Glu Asp Ile Val Phe
1               5                   10

<210> SEQ ID NO 26
<211> LENGTH: 9
<212> TYPE: PRT
<213> ORGANISM: Artificial
<220> FEATURE:
<223> OTHER INFORMATION: an artificially synthesized peptide

<400> SEQUENCE: 26

Phe Leu Gln Gly His Gly Asn Asn Val
1               5

<210> SEQ ID NO 27
<211> LENGTH: 9
<212> TYPE: PRT
<213> ORGANISM: Artificial
<220> FEATURE:
<223> OTHER INFORMATION: an artificially synthesized peptide

<400> SEQUENCE: 27

Ile Leu Ala Asn Thr Leu Phe Gln Cys
1               5

<210> SEQ ID NO 28
<211> LENGTH: 9
<212> TYPE: PRT
<213> ORGANISM: Artificial
<220> FEATURE:
<223> OTHER INFORMATION: an artificially synthesized peptide

<400> SEQUENCE: 28

Ile Thr Gln Glu Gly Val His Phe Val
1               5

<210> SEQ ID NO 29
<211> LENGTH: 9
<212> TYPE: PRT
<213> ORGANISM: Artificial
<220> FEATURE:
<223> OTHER INFORMATION: an artificially synthesized peptide

<400> SEQUENCE: 29
```

Lys Met Asn Pro Arg Thr Lys Leu Leu
1               5

<210> SEQ ID NO 30
<211> LENGTH: 9
<212> TYPE: PRT
<213> ORGANISM: Artificial
<220> FEATURE:
<223> OTHER INFORMATION: an artificially synthesized peptide

<400> SEQUENCE: 30

Met Ile Tyr Pro Leu Gly Cys Thr Val
1               5

<210> SEQ ID NO 31
<211> LENGTH: 9
<212> TYPE: PRT
<213> ORGANISM: Artificial
<220> FEATURE:
<223> OTHER INFORMATION: an artificially synthesized peptide

<400> SEQUENCE: 31

Arg Leu Met Tyr Val Ile Asn Asn Ala
1               5

<210> SEQ ID NO 32
<211> LENGTH: 9
<212> TYPE: PRT
<213> ORGANISM: Artificial
<220> FEATURE:
<223> OTHER INFORMATION: an artificially synthesized peptide

<400> SEQUENCE: 32

Leu Leu Val Gly Ser Gly Ala Gly Leu
1               5

<210> SEQ ID NO 33
<211> LENGTH: 9
<212> TYPE: PRT
<213> ORGANISM: Artificial
<220> FEATURE:
<223> OTHER INFORMATION: an artificially synthesized peptide

<400> SEQUENCE: 33

Lys Ile Trp Pro Thr Glu Cys Gln Thr
1               5

<210> SEQ ID NO 34
<211> LENGTH: 9
<212> TYPE: PRT
<213> ORGANISM: Artificial
<220> FEATURE:
<223> OTHER INFORMATION: an artificially synthesized peptide

<400> SEQUENCE: 34

Gln Leu Gln Gly Gly Ile Thr Ser Ile
1               5

<210> SEQ ID NO 35
<211> LENGTH: 9
<212> TYPE: PRT
<213> ORGANISM: Artificial
<220> FEATURE:
<223> OTHER INFORMATION: an artificially synthesized peptide

<400> SEQUENCE: 35

Ala Leu Ala Phe Ser Pro Asn Asp Leu

```
<210> SEQ ID NO 36
<211> LENGTH: 9
<212> TYPE: PRT
<213> ORGANISM: Artificial
<220> FEATURE:
<223> OTHER INFORMATION: an artificially synthesized peptide

<400> SEQUENCE: 36

Lys Leu Leu Thr Asp Val Gly Pro Ala
1               5

<210> SEQ ID NO 37
<211> LENGTH: 9
<212> TYPE: PRT
<213> ORGANISM: Artificial
<220> FEATURE:
<223> OTHER INFORMATION: an artificially synthesized peptide

<400> SEQUENCE: 37

Ser Leu Ser Gly Ser Ile Asn Gly Met
1               5

<210> SEQ ID NO 38
<211> LENGTH: 10
<212> TYPE: PRT
<213> ORGANISM: Artificial
<220> FEATURE:
<223> OTHER INFORMATION: an artificially synthesized peptide

<400> SEQUENCE: 38

Ile Leu Trp Asp Tyr Lys Asn Arg Glu Leu
1               5                   10

<210> SEQ ID NO 39
<211> LENGTH: 10
<212> TYPE: PRT
<213> ORGANISM: Artificial
<220> FEATURE:
<223> OTHER INFORMATION: an artificially synthesized peptide

<400> SEQUENCE: 39

Ile Leu Ala Asn Thr Leu Phe Gln Cys Val
1               5                   10

<210> SEQ ID NO 40
<211> LENGTH: 10
<212> TYPE: PRT
<213> ORGANISM: Artificial
<220> FEATURE:
<223> OTHER INFORMATION: an artificially synthesized peptide

<400> SEQUENCE: 40

Lys Val Trp Asp Tyr Asn Glu Gly Glu Val
1               5                   10

<210> SEQ ID NO 41
<211> LENGTH: 10
<212> TYPE: PRT
<213> ORGANISM: Artificial
<220> FEATURE:
<223> OTHER INFORMATION: an artificially synthesized peptide

<400> SEQUENCE: 41

Gly Leu Leu Val Gly Ser Gly Ala Gly Leu
1               5                   10
```

<210> SEQ ID NO 42
<211> LENGTH: 10
<212> TYPE: PRT
<213> ORGANISM: Artificial
<220> FEATURE:
<223> OTHER INFORMATION: an artificially synthesized peptide

<400> SEQUENCE: 42

Gly Leu Asn Val Gly Asn Ala Thr Asn Val
1               5                   10

<210> SEQ ID NO 43
<211> LENGTH: 10
<212> TYPE: PRT
<213> ORGANISM: Artificial
<220> FEATURE:
<223> OTHER INFORMATION: an artificially synthesized peptide

<400> SEQUENCE: 43

Met Ile Leu Ala Asn Thr Leu Phe Gln Cys
1               5                   10

<210> SEQ ID NO 44
<211> LENGTH: 10
<212> TYPE: PRT
<213> ORGANISM: Artificial
<220> FEATURE:
<223> OTHER INFORMATION: an artificially synthesized peptide

<400> SEQUENCE: 44

Phe Leu Val Gly Thr Glu Glu Ser His Ile
1               5                   10

<210> SEQ ID NO 45
<211> LENGTH: 10
<212> TYPE: PRT
<213> ORGANISM: Artificial
<220> FEATURE:
<223> OTHER INFORMATION: an artificially synthesized peptide

<400> SEQUENCE: 45

Tyr Ile Ala Ser Gly Gln Val Thr Phe Met
1               5                   10

<210> SEQ ID NO 46
<211> LENGTH: 10
<212> TYPE: PRT
<213> ORGANISM: Artificial
<220> FEATURE:
<223> OTHER INFORMATION: an artificially synthesized peptide

<400> SEQUENCE: 46

Ala Ile Leu Arg Trp Lys Tyr Pro Tyr Thr
1               5                   10

<210> SEQ ID NO 47
<211> LENGTH: 10
<212> TYPE: PRT
<213> ORGANISM: Artificial
<220> FEATURE:
<223> OTHER INFORMATION: an artificially synthesized peptide

<400> SEQUENCE: 47

Phe Met Gly Phe Lys Ala Asp Ile Ile Leu
1               5                   10

<210> SEQ ID NO 48

```
<211> LENGTH: 10
<212> TYPE: PRT
<213> ORGANISM: Artificial
<220> FEATURE:
<223> OTHER INFORMATION: an artificially synthesized peptide

<400> SEQUENCE: 48

Thr Leu Ile Ala Thr Cys His Phe Asp Ala
1               5                   10

<210> SEQ ID NO 49
<211> LENGTH: 10
<212> TYPE: PRT
<213> ORGANISM: Artificial
<220> FEATURE:
<223> OTHER INFORMATION: an artificially synthesized peptide

<400> SEQUENCE: 49

Gln Val Ala Glu Leu Glu Leu Asp Ala Val
1               5                   10

<210> SEQ ID NO 50
<211> LENGTH: 10
<212> TYPE: PRT
<213> ORGANISM: Artificial
<220> FEATURE:
<223> OTHER INFORMATION: an artificially synthesized peptide

<400> SEQUENCE: 50

Phe Val Thr Gly Gly Asn Asp His Leu Val
1               5                   10

<210> SEQ ID NO 51
<211> LENGTH: 10
<212> TYPE: PRT
<213> ORGANISM: Artificial
<220> FEATURE:
<223> OTHER INFORMATION: an artificially synthesized peptide

<400> SEQUENCE: 51

Ser Leu His Lys Gly Lys Ile Glu Ala Leu
1               5                   10

<210> SEQ ID NO 52
<211> LENGTH: 10
<212> TYPE: PRT
<213> ORGANISM: Artificial
<220> FEATURE:
<223> OTHER INFORMATION: an artificially synthesized peptide

<400> SEQUENCE: 52

Asn Met Thr Cys His Gly Ile Asp Phe Met
1               5                   10

<210> SEQ ID NO 53
<211> LENGTH: 10
<212> TYPE: PRT
<213> ORGANISM: Artificial
<220> FEATURE:
<223> OTHER INFORMATION: an artificially synthesized peptide

<400> SEQUENCE: 53

Tyr Leu Gly Thr Thr Thr Gly Asp Ile Leu
1               5                   10

<210> SEQ ID NO 54
<211> LENGTH: 10
<212> TYPE: PRT
```

-continued

```
<213> ORGANISM: Artificial
<220> FEATURE:
<223> OTHER INFORMATION: an artificially synthesized peptide

<400> SEQUENCE: 54

Lys Met Asn Pro Arg Thr Lys Leu Leu Thr
1               5                   10

<210> SEQ ID NO 55
<211> LENGTH: 10
<212> TYPE: PRT
<213> ORGANISM: Artificial
<220> FEATURE:
<223> OTHER INFORMATION: an artificially synthesized peptide

<400> SEQUENCE: 55

Val Ile Asn Asn Ala His Arg Ile Gly Val
1               5                   10

<210> SEQ ID NO 56
<211> LENGTH: 10
<212> TYPE: PRT
<213> ORGANISM: Artificial
<220> FEATURE:
<223> OTHER INFORMATION: an artificially synthesized peptide

<400> SEQUENCE: 56

Ala Ile Asn Thr Lys Glu Gln Asn Phe Leu
1               5                   10

<210> SEQ ID NO 57
<211> LENGTH: 10
<212> TYPE: PRT
<213> ORGANISM: Artificial
<220> FEATURE:
<223> OTHER INFORMATION: an artificially synthesized peptide

<400> SEQUENCE: 57

Ile Gln Leu Gln Gly Gly Ile Thr Ser Ile
1               5                   10

<210> SEQ ID NO 58
<211> LENGTH: 10
<212> TYPE: PRT
<213> ORGANISM: Artificial
<220> FEATURE:
<223> OTHER INFORMATION: an artificially synthesized peptide

<400> SEQUENCE: 58

Leu Ile Ala Thr Cys His Phe Asp Ala Val
1               5                   10

<210> SEQ ID NO 59
<211> LENGTH: 10
<212> TYPE: PRT
<213> ORGANISM: Artificial
<220> FEATURE:
<223> OTHER INFORMATION: an artificially synthesized peptide

<400> SEQUENCE: 59

Gly Glu Gly Glu Val Arg Val Trp Gln Ile
1               5                   10

<210> SEQ ID NO 60
<211> LENGTH: 10
<212> TYPE: PRT
<213> ORGANISM: Artificial
<220> FEATURE:
```

<223> OTHER INFORMATION: an artificially synthesized peptide

<400> SEQUENCE: 60

Ile Val Phe Pro Phe Gly Thr Ala Glu Leu
1               5                   10

<210> SEQ ID NO 61
<211> LENGTH: 10
<212> TYPE: PRT
<213> ORGANISM: Artificial
<220> FEATURE:
<223> OTHER INFORMATION: an artificially synthesized peptide

<400> SEQUENCE: 61

Leu Val Gly Ser Gly Ala Gly Leu Leu Val
1               5                   10

<210> SEQ ID NO 62
<211> LENGTH: 10
<212> TYPE: PRT
<213> ORGANISM: Artificial
<220> FEATURE:
<223> OTHER INFORMATION: an artificially synthesized peptide

<400> SEQUENCE: 62

Leu Ala Phe Ser Pro Asn Asp Leu Tyr Leu
1               5                   10

<210> SEQ ID NO 63
<211> LENGTH: 2207
<212> TYPE: DNA
<213> ORGANISM: Homo sapiens
<220> FEATURE:
<221> NAME/KEY: CDS
<222> LOCATION: (70)..(1932)

<400> SEQUENCE: 63

```
gttaccataa cgaccagaag acgctgcagc cactagggag gagagcaaag taatcagaac      60 ctcccaagg atg gat aac aaa att tcg ccg gag gcc caa gtg gcg gag ctg     111
           Met Asp Asn Lys Ile Ser Pro Glu Ala Gln Val Ala Glu Leu
             1               5                   10 gaa ctt gac gcc gtg atc ggc ttc aat gga cat gtg ccc act ggt ctc       159
Glu Leu Asp Ala Val Ile Gly Phe Asn Gly His Val Pro Thr Gly Leu
 15                  20                  25                  30 aaa tgc cat cct gac cag gag cat atg att tat cct ctt ggt tgc aca       207
Lys Cys His Pro Asp Gln Glu His Met Ile Tyr Pro Leu Gly Cys Thr
                 35                  40                  45 gtc ctc att cag gca ata aat act aaa gag cag aac ttc cta cag ggt       255
Val Leu Ile Gln Ala Ile Asn Thr Lys Glu Gln Asn Phe Leu Gln Gly
             50                  55                  60 cat ggc aac aac gtc tcc tgc ttg gcc atc tcc agg tct gga gag tac       303
His Gly Asn Asn Val Ser Cys Leu Ala Ile Ser Arg Ser Gly Glu Tyr
         65                  70                  75 atc gcc tcc gga caa gtc aca ttc atg ggg ttc aag gca gac atc att       351
Ile Ala Ser Gly Gln Val Thr Phe Met Gly Phe Lys Ala Asp Ile Ile
 80                  85                  90 ttg tgg gat tat aag aac aga gag ctg ctt gct cgg ctg tcc ctt cac       399
Leu Trp Asp Tyr Lys Asn Arg Glu Leu Leu Ala Arg Leu Ser Leu His
 95                 100                 105                 110 aaa ggc aaa att gaa gct ctg gcc ttt tct cca aat gat ttg tac ttg       447
Lys Gly Lys Ile Glu Ala Leu Ala Phe Ser Pro Asn Asp Leu Tyr Leu
                115                 120                 125 gta tca cta gga ggc cca gat gac gga agt gtg gtg gtg tgg agc ata       495
Val Ser Leu Gly Gly Pro Asp Asp Gly Ser Val Val Val Trp Ser Ile
```

|     |     |
| --- | --- |
| gcc aag aga gat gcc atc tgt ggc agc cct gca gcc ggc ctc aat gtt<br>Ala Lys Arg Asp Ala Ile Cys Gly Ser Pro Ala Ala Gly Leu Asn Val<br>145               150               155 | 543 |
| ggc aat gcc acc aat gtg atc ttc tcc agg tgc cgg gat gag atg ttt<br>Gly Asn Ala Thr Asn Val Ile Phe Ser Arg Cys Arg Asp Glu Met Phe<br>160               165               170 | 591 |
| atg act gct gga aat ggg aca att cga gta tgg gaa ttg gat ctt cca<br>Met Thr Ala Gly Asn Gly Thr Ile Arg Val Trp Glu Leu Asp Leu Pro<br>175               180               185               190 | 639 |
| aat aga aaa atc tgg cca act gag tgc caa aca gga cag ttg aaa aga<br>Asn Arg Lys Ile Trp Pro Thr Glu Cys Gln Thr Gly Gln Leu Lys Arg<br>               195               200               205 | 687 |
| ata gtc atg agt att gga gtg gat gat gat gat agc ttt ttc tac ctt<br>Ile Val Met Ser Ile Gly Val Asp Asp Asp Asp Ser Phe Phe Tyr Leu<br>          210               215               220 | 735 |
| ggc acc acg act gga gat att cta aaa atg aac ccc agg act aaa ctg<br>Gly Thr Thr Thr Gly Asp Ile Leu Lys Met Asn Pro Arg Thr Lys Leu<br>         225               230               235 | 783 |
| ctg aca gat gtt ggg cct gcg aag gac aaa ttc agt ttg gga gtg tca<br>Leu Thr Asp Val Gly Pro Ala Lys Asp Lys Phe Ser Leu Gly Val Ser<br>240               245               250 | 831 |
| gct atc agg tgc ctg aag atg ggg ggt ttg ttg gtg ggc tct gga gcc<br>Ala Ile Arg Cys Leu Lys Met Gly Gly Leu Leu Val Gly Ser Gly Ala<br>255               260               265               270 | 879 |
| gga ctg ctg gtc ttc tgt aaa agc cct ggc tac aaa ccc atc aag aag<br>Gly Leu Leu Val Phe Cys Lys Ser Pro Gly Tyr Lys Pro Ile Lys Lys<br>               275               280               285 | 927 |
| att cag tta caa ggc ggc atc act tct atc aca ctt cga gga gaa gga<br>Ile Gln Leu Gln Gly Gly Ile Thr Ser Ile Thr Leu Arg Gly Glu Gly<br>         290               295               300 | 975 |
| cac cag ttt ctc gta gga aca gaa gaa tcg cac att tat cgt gtc agc<br>His Gln Phe Leu Val Gly Thr Glu Glu Ser His Ile Tyr Arg Val Ser<br>         305               310               315 | 1023 |
| ttc acg gat ttc aaa gag acg ctc ata gcg act tgt cac ttt gat gct<br>Phe Thr Asp Phe Lys Glu Thr Leu Ile Ala Thr Cys His Phe Asp Ala<br>320               325               330 | 1071 |
| gtc gag gat att gtc ttt cca ttt ggc act gct gag cta ttt gca acc<br>Val Glu Asp Ile Val Phe Pro Phe Gly Thr Ala Glu Leu Phe Ala Thr<br>335               340               345               350 | 1119 |
| tgt gcc aag aag gat atc agg gtg tgg cac aca tca tcc aac agg gag<br>Cys Ala Lys Lys Asp Ile Arg Val Trp His Thr Ser Ser Asn Arg Glu<br>               355               360               365 | 1167 |
| ctg ctg cgg atc acc gtg ccc aac atg acc tgc cac ggc atc gac ttc<br>Leu Leu Arg Ile Thr Val Pro Asn Met Thr Cys His Gly Ile Asp Phe<br>         370               375               380 | 1215 |
| atg agg gac ggc aaa agc atc att tca gca tgg aac gac ggt aaa atc<br>Met Arg Asp Gly Lys Ser Ile Ile Ser Ala Trp Asn Asp Gly Lys Ile<br>         385               390               395 | 1263 |
| cga gcc ttc gcc cca gag aca ggc cga ctg atg tat gtc att aac aat<br>Arg Ala Phe Ala Pro Glu Thr Gly Arg Leu Met Tyr Val Ile Asn Asn<br>400               405               410 | 1311 |
| gct cac agg atc ggc gtc acc gcc atc gcc acc acc agt gac tgt aaa<br>Ala His Arg Ile Gly Val Thr Ala Ile Ala Thr Thr Ser Asp Cys Lys<br>415               420               425               430 | 1359 |
| agg gtc atc agt ggc ggt ggg gaa ggg gag gtg agg gta tgg cag ata<br>Arg Val Ile Ser Gly Gly Gly Glu Gly Glu Val Arg Val Trp Gln Ile<br>               435               440               445 | 1407 |
| ggc tgt cag acc cag aag ctg gag gag gcc ctg aag gaa cac aag tca<br>Gly Cys Gln Thr Gln Lys Leu Glu Glu Ala Leu Lys Glu His Lys Ser | 1455 |

-continued

|  |  |  |  |  |  | 450 |  |  |  |  |  | 455 |  |  |  |  |  | 460 |  |  |  |
|---|---|---|---|---|---|---|---|---|---|---|---|---|---|---|---|---|---|---|---|---|---|

```
tca gtg tcc tgc att agg gtg aag agg aac aac gag gag tgt gtc acc    1503
Ser Val Ser Cys Ile Arg Val Lys Arg Asn Asn Glu Glu Cys Val Thr
        465                 470                 475 gcc agc acc gat ggg act tgt atc att tgg gac ctt gtg cgt ctc agg    1551
Ala Ser Thr Asp Gly Thr Cys Ile Ile Trp Asp Leu Val Arg Leu Arg
    480                 485                 490 agg aat cag atg ata cta gcc aac acc tta ttc cag tgt gtg tgc tat    1599
Arg Asn Gln Met Ile Leu Ala Asn Thr Leu Phe Gln Cys Val Cys Tyr
495                 500                 505                 510 cac cct gag gag ttc cag atc atc acc agc gga aca gac aga aag att    1647
His Pro Glu Glu Phe Gln Ile Ile Thr Ser Gly Thr Asp Arg Lys Ile
                515                 520                 525 gct tac tgg gaa gta ttt gat ggg aca gta atc aga gaa ttg gaa ggt    1695
Ala Tyr Trp Glu Val Phe Asp Gly Thr Val Ile Arg Glu Leu Glu Gly
            530                 535                 540 tcc ctg tct ggg tcg ata aat ggc atg gat atc aca cag gaa ggg gtg    1743
Ser Leu Ser Gly Ser Ile Asn Gly Met Asp Ile Thr Gln Glu Gly Val
        545                 550                 555 cac ttt gtc aca ggt gga aat gac cat ctg gtc aaa gtt tgg gat tat    1791
His Phe Val Thr Gly Gly Asn Asp His Leu Val Lys Val Trp Asp Tyr
    560                 565                 570 aat gag ggt gaa gtg act cac gtt ggg gtg gga cac agt ggc aac atc    1839
Asn Glu Gly Glu Val Thr His Val Gly Val Gly His Ser Gly Asn Ile
575                 580                 585                 590 aca cgc atc cgc ata agt cca gga aat caa tat att gtt agt gta agt    1887
Thr Arg Ile Arg Ile Ser Pro Gly Asn Gln Tyr Ile Val Ser Val Ser
                595                 600                 605 gcc gat gga gcc att ttg cga tgg aag tac cca tat acc tcc tga        1932
Ala Asp Gly Ala Ile Leu Arg Trp Lys Tyr Pro Tyr Thr Ser
            610                 615                 620 agctgatgag atgtctctga gccttggcgt tgcacgcagt cctgttgaag actgagttta    1992
gataactcca acactagtct tcatttctca cagctctgtt tttgttcttg agtcaatttt    2052 tctcttttc tttatagaat gcattttata ttcttaaatt gcatattaaa attgaagtat     2112
gttcaagaat aatttgtgca gactctaatt agaactttta acattttgaa taaattctta   2172
gttgttggtt ttctgttata aaaaaaaaaa aaaaa                              2207
```

<210> SEQ ID NO 64
<211> LENGTH: 620
<212> TYPE: PRT
<213> ORGANISM: Homo sapiens

<400> SEQUENCE: 64

```
Met Asp Asn Lys Ile Ser Pro Glu Ala Gln Val Ala Glu Leu Glu Leu
1               5                   10                  15

Asp Ala Val Ile Gly Phe Asn Gly His Val Pro Thr Gly Leu Lys Cys
            20                  25                  30

His Pro Asp Gln Glu His Met Ile Tyr Pro Leu Gly Cys Thr Val Leu
        35                  40                  45

Ile Gln Ala Ile Asn Thr Lys Glu Gln Asn Phe Leu Gln Gly His Gly
    50                  55                  60

Asn Asn Val Ser Cys Leu Ala Ile Ser Arg Ser Gly Glu Tyr Ile Ala
65                  70                  75                  80

Ser Gly Gln Val Thr Phe Met Gly Phe Lys Ala Asp Ile Ile Leu Trp
                85                  90                  95

Asp Tyr Lys Asn Arg Glu Leu Leu Ala Arg Leu Ser Leu His Lys Gly
            100                 105                 110
```

```
Lys Ile Glu Ala Leu Ala Phe Ser Pro Asn Asp Leu Tyr Leu Val Ser
            115                 120                 125

Leu Gly Gly Pro Asp Asp Gly Ser Val Val Trp Ser Ile Ala Lys
        130                 135                 140

Arg Asp Ala Ile Cys Gly Ser Pro Ala Ala Gly Leu Asn Val Gly Asn
145                 150                 155                 160

Ala Thr Asn Val Ile Phe Ser Arg Cys Arg Asp Glu Met Phe Met Thr
                165                 170                 175

Ala Gly Asn Gly Thr Ile Arg Val Trp Glu Leu Asp Leu Pro Asn Arg
            180                 185                 190

Lys Ile Trp Pro Thr Glu Cys Gln Thr Gly Gln Leu Lys Arg Ile Val
        195                 200                 205

Met Ser Ile Gly Val Asp Asp Asp Ser Phe Phe Tyr Leu Gly Thr
    210                 215                 220

Thr Thr Gly Asp Ile Leu Lys Met Asn Pro Arg Thr Lys Leu Leu Thr
225                 230                 235                 240

Asp Val Gly Pro Ala Lys Asp Lys Phe Ser Leu Gly Val Ser Ala Ile
                245                 250                 255

Arg Cys Leu Lys Met Gly Gly Leu Leu Val Gly Ser Gly Ala Gly Leu
            260                 265                 270

Leu Val Phe Cys Lys Ser Pro Gly Tyr Lys Pro Ile Lys Lys Ile Gln
        275                 280                 285

Leu Gln Gly Gly Ile Thr Ser Ile Thr Leu Arg Gly Glu Gly His Gln
290                 295                 300

Phe Leu Val Gly Thr Glu Glu Ser His Ile Tyr Arg Val Ser Phe Thr
305                 310                 315                 320

Asp Phe Lys Glu Thr Leu Ile Ala Thr Cys His Phe Asp Ala Val Glu
            325                 330                 335

Asp Ile Val Phe Pro Phe Gly Thr Ala Glu Leu Phe Ala Thr Cys Ala
        340                 345                 350

Lys Lys Asp Ile Arg Val Trp His Thr Ser Ser Asn Arg Glu Leu Leu
355                 360                 365

Arg Ile Thr Val Pro Asn Met Thr Cys His Gly Ile Asp Phe Met Arg
    370                 375                 380

Asp Gly Lys Ser Ile Ile Ser Ala Trp Asn Asp Gly Lys Ile Arg Ala
385                 390                 395                 400

Phe Ala Pro Glu Thr Gly Arg Leu Met Tyr Val Ile Asn Asn Ala His
            405                 410                 415

Arg Ile Gly Val Thr Ala Ile Ala Thr Thr Ser Asp Cys Lys Arg Val
        420                 425                 430

Ile Ser Gly Gly Gly Glu Gly Glu Val Arg Val Trp Gln Ile Gly Cys
    435                 440                 445

Gln Thr Gln Lys Leu Glu Glu Ala Leu Lys Glu His Lys Ser Ser Val
450                 455                 460

Ser Cys Ile Arg Val Lys Arg Asn Asn Glu Glu Cys Val Thr Ala Ser
465                 470                 475                 480

Thr Asp Gly Thr Cys Ile Ile Trp Asp Leu Val Arg Leu Arg Arg Asn
            485                 490                 495

Gln Met Ile Leu Ala Asn Thr Leu Phe Gln Cys Val Cys Tyr His Pro
        500                 505                 510

Glu Glu Phe Gln Ile Ile Thr Ser Gly Thr Asp Arg Lys Ile Ala Tyr
    515                 520                 525

Trp Glu Val Phe Asp Gly Thr Val Ile Arg Glu Leu Glu Gly Ser Leu
```

```
                530                 535                 540
Ser Gly Ser Ile Asn Gly Met Asp Ile Thr Gln Glu Gly Val His Phe
545                 550                 555                 560

Val Thr Gly Gly Asn Asp His Leu Val Lys Val Trp Asp Tyr Asn Glu
                565                 570                 575

Gly Glu Val Thr His Val Gly Val Gly His Ser Gly Asn Ile Thr Arg
            580                 585                 590

Ile Arg Ile Ser Pro Gly Asn Gln Tyr Ile Val Ser Val Ser Ala Asp
                595                 600                 605

Gly Ala Ile Leu Arg Trp Lys Tyr Pro Tyr Thr Ser
610                 615                 620

<210> SEQ ID NO 65
<211> LENGTH: 22
<212> TYPE: DNA
<213> ORGANISM: Artificial
<220> FEATURE:
<223> OTHER INFORMATION: Artificial sequence

<400> SEQUENCE: 65
gtctaccagg cattcgcttc at                                          22

<210> SEQ ID NO 66
<211> LENGTH: 24
<212> TYPE: DNA
<213> ORGANISM: Artificial
<220> FEATURE:
<223> OTHER INFORMATION: Artificial sequence

<400> SEQUENCE: 66
tcagctggac cacagccgca gcgt                                        24

<210> SEQ ID NO 67
<211> LENGTH: 21
<212> TYPE: DNA
<213> ORGANISM: Artificial
<220> FEATURE:
<223> OTHER INFORMATION: Artificial sequence

<400> SEQUENCE: 67
tcagaaatcc tttctcttga c                                           21

<210> SEQ ID NO 68
<211> LENGTH: 24
<212> TYPE: DNA
<213> ORGANISM: Artificial
<220> FEATURE:
<223> OTHER INFORMATION: Artificial sequence

<400> SEQUENCE: 68
ctagcctctg gaatcctttc tctt                                        24
```

WDRPUH EPITOPE PEPTIDES AND VACCINES CONTAINING THE SAME

The present application is a U.S. National Stage Application of PCT/JP2009/006573, filed Dec. 3, 2009, which claims the benefit of U.S. Provisional Applications No. 61/200,962, filed on Dec. 5, 2008, and 61/209,704, filed on Mar. 9, 2009, the entire contents of which are incorporated by reference herein in their entirety.

TECHNICAL FIELD

The present invention relates to the field of biological science, more specifically to the field of cancer therapy. In particular, the present invention relates to novel peptides that are extremely effective as cancer vaccines, and drugs for treating and preventing tumors.

BACKGROUND ART

It has been demonstrated that CD8 positive cytotoxic T lymphocytes (CTLs) recognize epitope peptides derived from the tumor-associated antigens (TAAs) found on major histocompatibility complex (MHC) class 1 molecules, and then kill the tumor cells. Since the discovery of the melanoma antigen (MAGE) family as the first example of TAAs, many other TAAs have been discovered, primarily through immunological approaches (Boon T, Int J Cancer 1993 May 8, 54(2): 177-80; Boon T & van der Bruggen P, J Exp Med 1996 Mar. 1, 183(3): 725-9). Some of these TAAs are currently undergoing clinical development as immunotherapeutic targets.

Identification of new TAAs, capable of inducing potent and specific anti-tumor immune responses, warrants further development and clinical application of peptide vaccination strategies for various types of cancer (Harris C C, J Natl Cancer Inst 1996 Oct. 16, 88(20): 1442-55; Butterfield L H et al., Cancer Res 1999 Jul. 1, 59(13): 3134-42; Vissers J L et al., Cancer Res 1999 Nov. 1, 59(21): 5554-9; van der Burg S H et al., J Immunol 1996 May 1, 156(9): 3308-14; Tanaka F et al., Cancer Res 1997 Oct. 15, 57(20): 4465-8; Fujie T et al., Int J Cancer 1999 Jan. 18, 80(2): 169-72; Kikuchi M et al., Int J Cancer 1999 May 5, 81(3): 459-66; Oiso M et al., Int J Cancer 1999 May 5, 81(3): 387-94). To date, there have been several reports of clinical trials using these tumor-associated antigen derived peptides. Unfortunately, only a low objective response rate has been observed in these cancer vaccine trials so far (Belli F et al., J Clin Oncol 2002 Oct. 15, 20(20): 4169-80; Coulie P G et al., Immunol Rev 2002 October, 188: 33-42; Rosenberg S A et al., Nat Med 2004 September, 10(9): 909-15).

As a target for immunotherapy, TAAs indispensable for the proliferation and survival of cancer cells are suited, because the use of such TAAs may minimize the well-described risk of immune escape of cancer cells attributable to deletion, mutation, or down-regulation of TAAs as a consequence of therapeutically driven immune selection.

WDRPUH was identified as a novel WD repeat protein that is upregulated in hepatocellular carcinoma through gene expression profile using a genome-wide cDNA microarray containing 23,040 genes (Silva et al., Neoplasia 2005 April; 7(4):348-55, WO 2003/104276). WD repeat-containing proteins have been reported to play crucial roles in a wide range of physiologic functions, including signal transduction, RNA processing (Bjorn et al., Mol Cell Biol. 1989 September; 9(9):3698-709), remodeling of the cytoskeleton (Vaisman et al., Mol Gen Genet. 1995 Apr. 20; 247(2):123-36), regulation of vesicular traffic (Pryer et al., J. Cell Biol. 1993 February; 120(4):865-75), and cell division (Feldman et al., Cell. 1997 Oct. 17; 91(2):221-30). Northern blot analysis demonstrated that WDRPUH was over-expressed at a significantly high level in a great majority of hepatocellular carcinoma, but was not expressed in normal organs except for testis. Furthermore, suppression of WDRPUH expression by siRNA was shown to significantly inhibit growth of human hepatocellular carcinoma cell lines (Silva et al., Neoplasia 2005 April; 7(4):348-55, WO 2003/104276).

CITATION LIST

Patent Literature

[PTL 1] WO 2003/104276

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20) 1442-55
[NPL 4] Butterfield L H et al., Cancer Res 1999 Jul. 1, 59(13), 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Silva et al., Neoplasia 2005 April; 7(4):348-55
[NPL 15] Bjorn et al., Mol Cell Biol. 1989 September; 9(9): 3698-709
[NPL 16] Vaisman et al., Mol Gen Genet. 1995 Apr. 20; 247(2):123-36)
[NPL 17] Pryer et al., J. Cell Biol. 1993 February; 120(4): 865-75
[NPL 18] Feldman et al., Cell. 1997 Oct. 17; 91(2):221-30

SUMMARY OF INVENTION

The present invention is based in part on the discovery of suitable targets of immunotherapy. Because TAAs are generally perceived by the immune system as "self" and therefore often have no innate immunogenicity, the discovery of appropriate targets is of extreme importance. As noted above, recognizing that WDRPUH (SEQ ID NO: 64 encoded by the gene of GenBank Accession No. NM_145054 (SEQ ID NO: 63)) has been identified as up-regulated in cancer tissue of hepatocellular carcinoma, WDRPUH is a candidate target for immunotherapy.

The present invention is based, at least in part, on the identification of specific epitope peptides of the gene products of WDRPUH which possess the ability to induce CTLs specific to WDRPUH. As discussed in detail below, peripheral blood mononuclear cells (PBMCs) obtained from a healthy donor were stimulated using HLA-A*2402 or HLA-A*0201 binding candidate peptides derived from WDRPUH. CTL lines with specific cytotoxicity against HLA-A24 or HLA-A2 positive target cells pulsed with each of candidate peptides were then established. The results demonstrated that the peptides are HLA-A24 or HLA-A2 restricted epitope peptides that can induce potent and specific immune responses against cells expressing WDRPUH on the surface. Further, it indicated that WDRPUH is strongly immunogenic and the epitopes thereof are effective targets for tumor immunotherapy.

Accordingly, it is an object of the present invention to provide isolated peptides that bind to the HLA antigen, which peptides consist of WDRPUH (SEQ ID NO: 64) or a fragment of WDRPUH. Such peptides are expected to have CTL inducibility and can be used for inducing CTLs in ex vivo or for administration to a subject for inducing immune responses against cancers such as hepatocellular carcinoma. The peptides may be nonapeptides or decapeptides preferably consisting of the amino acid sequence selected from among SEQ ID NOs: 1, 2, 3, 4, 16, 17, 30, 31, 34, 36, 37, 40, 41, 45, 49, 55, 57 and 61, which show strong CTL inducibility.

In addition, the present invention contemplates modified peptides, having an amino acid sequence of SEQ ID NOs: 1, 2, 3, 4, 16, 17, 30, 31, 34, 36, 37, 40, 41, 45, 49, 55, 57 and 61 wherein one, two or more amino acids are substituted, inserted, deleted or added, so long as the modified peptides retain the original CTL inducibility.

It is a further object of the present invention to provide isolated polynucleotides encoding any of the peptides of the present invention. These polynucleotides can be used for inducing antigen-expressing cells (APCs) with CTL inducibility or for administration to a subject to induce immune responses against the present peptides and thus finally against cancers.

When administered to a subject, the present peptides are presented on the surface of APCs and then induce CTLs targeting the respective peptides. Therefore, it is an object of the present invention to provide agents containing any of the peptides or polynucleotides of the present invention for inducing CTLs. These agents containing any of the peptides or polynucleotides of the present invention can be used for the treatment and/or prophylaxis of cancers, such as hepatocellular carcinoma, and/or the prevention of postoperative recurrence thereof. Thus, it is yet another object of the present invention to provide pharmaceutical agents for the treatment and/or prophylaxis of cancers, and/or prevention of postoperative recurrence thereof, which contains any of the peptides or polynucleotides of the present invention. The present agents or pharmaceutical agents may also contain, as the active ingredient, APCs or exosomes which present any of the present peptides instead of or in addition to the present peptides or polynucleotides.

The peptides or polynucleotides of the present invention have the ability to induce APCs which present, on its surface, a complex of an HLA antigen and the present peptide. For example, the induction can be achieved by contacting APCs derived from a subject with a peptide of the present invention or introducing a polynucleotide encoding a peptide of the present invention into APCs. Such APCs have high CTL inducibility against the target peptides and are useful for cancer immunotherapy. Therefore, it is a further object of the present invention to provide methods for inducing APCs with CTL inducibility and APCs obtained by the methods.

It is yet another object of the present invention to provide methods for inducing CTLs, which methods contain the step of co-culturing CD8-positive cells with APCs or exosomes presenting a peptide of the present invention on its surface or the step of introducing a polynucleotide into a T cell, which polynucleotide encodes a T cell receptor (TCR) subunit polypeptide binding to a peptide of the present invention. The CTLs obtained by the methods are useful for treating and/or preventing cancers, such as hepatocellular carcinoma. Therefore, it is a further object of the present invention to provide CTLs obtained by any of the present methods.

Another object of the present invention to provide methods for inducing immune response against cancers, which methods contain the step of administering an agent containing any of the WDRPUH polypeptides, polynucleotides encoding WDRPUH polypeptides, exosomes or the APCs presenting WDRPUH polypeptides of the present invention.

The present invention find use for application to any diseases related to WDRPUH over-expression including, but are not limited to, cancer, particularly hepatocellular carcinoma.

It is to be understood that both the foregoing summary of the invention and the following detailed description are of exemplified embodiments, and not restrictive of the invention or other alternate embodiments of the invention.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 1 includes a series of photographs depicting the results of IFN-gamma ELISPOT assay on CTLs that were induced with peptides derived from WDRPUH. The CTLs in well numbers #3 and #6 stimulated with WDRPUH-A24-9-40 (SEQ ID NO: 1) (a), #8 with WDRPUH-A24-9-314 (SEQ ID NO: 2) (b), #2 and #6 with WDRPUH-A24-9-509 (SEQ ID NO: 3) (c), #1, #2 and #5 with WDRPUH-A24-9-339 (SEQ ID NO: 4) (d), #2, #3, #4, #6, #7 and #8 with WDRPUH-A24-10-409 (SEQ ID NO: 16) (e) and #5, #6 and #8 with WDRPUH-A24-10-40 (SEQ ID NO: 17) (f) showed potent IFN-gamma production as compared with control, respectively. The cells in the wells denoted with a rectangular box were expanded to establish CTL lines. In the figure, "+" indicates that the cells in the wells were pulsed with appropriate peptides, and "−" indicates that the cells had not been pulsed with any peptides.

FIG. 2 includes a series of line graphs depicting IFN-gamma production of CTL lines stimulated with WDRPUH-A24-9-40 (SEQ ID NO: 1) (a), WDRPUH-A24-9-314 (SEQ ID NO: 2) (b), WDRPUH-A24-9-509 (SEQ ID NO: 3) (c), WDRPUH-A24-9-339 (SEQ ID NO: 4) (d), WDRPUH-A24-10-409 (SEQ ID NO: 16) (e) and WDRPUH-A24-10-40 (SEQ ID NO: 17) (f) with IFN-gamma ELISA assay. CTL lines established by stimulation with each of the peptides showed potent IFN-gamma production as compared with control. In the figure, "+" indicates that the cells in the wells were pulsed with appropriate peptides, and "−" indicates that the cells had not been pulsed with any peptides.

FIG. 3 is composed of a line graph depicting specific CTL activity against target cells that exogenously express WDRPUH and HLA-A*2402. COS7 cells transfected with only HLA-A*2402 or with only the full length WDRPUH gene were prepared as control. The CTL line established with WDRPUH-A24-9-314 (SEQ ID NO: 2) showed specific CTL activity against COS7 cells transfected with both WDRPUH and HLA-A*2402 (black lozenge). In contrast, no significant specific CTL activity was detected against target cells expressing either HLA-A*2402 (triangle) or WDRPUH (circle).

FIG. 4a-h includes a series of photographs depicting the results of IFN-gamma ELISPOT assay on CTLs that were induced with peptides derived from WDRPUH. The CTLs in well numbers #2 and #7 stimulated with WDRPUH-A2-9-39 (SEQ ID NO: 30) (a), #2 with WDRPUH-A2-9-407 (SEQ ID NO: 31) (b), #3 with WDRPUH-A2-9-288 (SEQ ID NO: 34) (c), #6 with WDRPUH-A2-9-237 (SEQ ID NO: 36) (d), #4 with WDRPUH-A2-9-543 (SEQ ID NO: 37) (e), #4 with WDRPUH-A2-10-570 (SEQ ID NO: 40) (f), #2 and #8 with WDRPUH-A2-10-263 (SEQ ID NO: 41) (g), #5 with WDRPUH-A2-10-78 (SEQ ID NO: 45) (h) showed potent IFN-gamma production as compared with the control, respectively. The cells in the wells denoted with a rectangular box were expanded to establish CTL lines. In the figure, "+" indicates that the cells in the wells were pulsed with appropriate peptides, and "−" indicates that the cells had not been pulsed with any peptides.

FIG. 4i-l includes a series of photographs depicting the results of IFN-gamma ELISPOT assay on CTLs that were induced with peptides derived from WDRPUH. The CTLs in well numbers #2 stimulated with WDRPUH-A2-10-10 (SEQ ID NO: 49) (i), #6 with WDRPUH-A2-10-411 (SEQ ID NO: 55) (j), #7 with WDRPUH-A2-10-287 (SEQ ID NO: 57) (k) and #6 with WDRPUH-A2-10-265 (SEQ ID NO: 61) (l) showed potent IFN-gamma production as compared with the control, respectively. The cells in the wells denoted with a rectangular box were expanded to establish CTL lines. In the figure, "+" indicates that the cells in the wells were pulsed with appropriate peptides, and "−" indicates that the cells had not been pulsed with any peptides.

FIGS. 5a and b are composed of line graphs depicting the IFN-gamma production of CTL lines stimulated with SEQ ID NO: 30 (a) and SEQ ID NO: 34 (b) detected by IFN-gamma ELISA assay. CTL lines established by stimulation with each peptide showed potent IFN-gamma production as compared with the control. In the figure, "+" indicates that the cells in the wells were pulsed with appropriate peptides, and "−" indicates that the cells had not been pulsed with any peptides.

FIGS. 5c and 5d depict the IFN-gamma production of the CTL clones established by limiting dilution from the CTL lines stimulated with SEQ ID NO: 30 (c) and SEQ ID NO: 34 (d). The results depicted herein demonstrate that the CTL clones established by stimulation with SEQ ID NO: 30 (c) and SEQ ID NO: 34 (d) showed potent IFN-gamma production as compared with the control. In the figure, "+" indicates that the cells in the wells were pulsed with SEQ ID NO: 30 (c) and SEQ ID NO: 34 (d) and "−" indicates that the cells had not been with any peptides.

FIG. 5e is composed of a line graph depicting specific CTL activity against the target cells that exogenously express WDRPUH and HLA-A*0201. COS7 cells transfected with only HLA-A*0201 or with only the full length WDRPUH gene were prepared as controls. The CTL clone established with WDRPUH-A2-9-288 (SEQ ID NO: 34) showed specific CTL activity against COS7 cells transfected with both WDRPUH and HLA-A*0201 (black lozenge). In contrast, no significant specific CTL activity was detected against target cells expressing either HLA-A*0201 (triangle) or WDRPUH (circle).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the descriptions is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "polynucleotides", "genes", "nucleotides" and "nucleic acids" are used interchangeably herein unless otherwise specifically indicated.

Unless otherwise defined, the term "cancer" refers to the cancers over-expressing the WDRPUH gene, examples of which include, but are not limited to, hepatocellular carcinoma.

Unless otherwise defined, the terms "cytotoxic T lymphocyte", "cytotoxic T cell" and "CTL" are used interchangeably herein and, unless otherwise specifically indicated, refer to a sub-group of T lymphocytes that are capable of recognizing non-self cells (e.g., tumor cells, virus-infected cells) and inducing the death of such cells.

Unless otherwise defined, the term "HLA-A2" contains the subtypes such as HLA-A0201 or HLA-A0206.

Unless otherwise defined, all technical and scientific terms used herein have the same meaning as commonly understood by one of ordinary skill in the art to which this invention belongs.

II. PEPTIDES

To demonstrate that peptides derived from WDRPUH function as an antigen recognized by CTLs, peptides derived from WDRPUH (SEQ ID NO: 64) were analyzed to determine whether they were antigen epitopes restricted by HLA-A24 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A24 binding peptides derived from WDRPUH were identified based on their binding affinities to HLA-A24. The following peptides are the candidate peptides:

```
WDRPUH-A24-9-40,      (SEQ ID NO: 1)

WDRPUH-A24-9-314,     (SEQ ID NO: 2)

WDRPUH-A24-9-509,     (SEQ ID NO: 3)

WDRPUH-A24-9-339,     (SEQ ID NO: 4)

WDRPUH-A24-10-409,    (SEQ ID NO: 16)
and

WDRPUH-A24-10-40.     (SEQ ID NO: 17)
```

Candidates of HLA-A02 binding peptides derived from WDRPUH were identified based on their binding affinities to HLA-A02. The following peptides are the candidate peptides:

```
WDRPUH-A2-9-39,       (SEQ ID NO: 30)

WDRPUH-A2-9-407,      (SEQ ID NO: 31)

WDRPUH-A2-9-288,      (SEQ ID NO: 34)

WDRPUH-A2-9-237,      (SEQ ID NO: 36)

WDRPUH-A2-9-543,      (SEQ ID NO: 37)

WDRPUH-A2-10-570,     (SEQ ID NO: 40)

WDRPUH-A2-10-263,     (SEQ ID NO: 41)

WDRPUH-A2-10-78,      (SEQ ID NO: 45)

WDRPUH-A2-10-10,      (SEQ ID NO: 49)

WDRPUH-A2-10-411,     (SEQ ID NO: 55)

WDRPUH-A2-10-287,     (SEQ ID NO: 57)
and

WDRPUH-A2-10-265.     (SEQ ID NO: 61)
```

These established CTLs show potent specific CTL activity against target cells pulsed with respective peptides. These results herein demonstrate that WDRPUH is an antigen recognized by CTLs and that the peptides may be epitope peptides of WDRPUH restricted by HLA-A24 or HLA-A2.

Since the WDRPUH gene is over expressed in cancer cells of such as hepatocellular carcinoma and not in most normal organs, it is a good target for immunotherapy. Thus, the present invention provides nonapeptides (peptides consisting of nine amino acid residues) and decapeptides (peptides consisting of ten amino acid residues) corresponding to CTL-recognized epitopes of WDRPUH. Particularly preferred examples of the peptides of the present invention include those peptides consisting of the amino acid sequence selected from among SEQ ID Nos: 1, 2, 3, 4, 16, 17, 30, 31, 34, 36, 37, 40, 41, 45, 49, 55, 57 and 61.

Generally, software programs presently available on the Internet, such as those described in Parker K C et al., J Immunol 1994 Jan. 1, 152(1): 163-75, can be used to calculate the binding affinities between various peptides and HLA antigens in silico. Binding affinity with HLA antigens can be measured as described, for example, in the reference to Parker K C et al., J Immunol 1994 Jan. 1, 152(1): 163-75; and Kuzushima P K et al., Blood 2001, 98(6): 1872-81. The methods for determining binding affinity are described, for example, in: Journal of Immunological Methods, 1995, 185: 181-190; Protein Science, 2000, 9: 1838-1846. Therefore, one can select fragments of WDRPUH, which have high binding affinity with HLA antigens using such software programs. Thus, the present invention encompasses peptides consisting of any fragments derived from WDRPUH, which bind with HLA antigens identified using such known programs. Furthermore, the present peptide may also consist of the full length of WDRPUH.

The peptides of the present invention can be flanked with additional amino acid residues so long as the resulting peptide retains its CTL inducibility. The particular amino acid residues flanking the peptides of the present invention can be composed of any kind of amino acids so long as they do not impair the CTL inducibility of the original peptide. Thus, the present invention also provides peptides having binding ability to HLA antigens and containing amino acid sequences derived from WDRPUH. Such peptides are typically less than about 40 amino acids, often less than about 20 amino acids, usually less than about 15 amino acids.

In general, the modification of one, two or more amino acids in a peptide will not influence the function of the peptide, and in some cases will even enhance the desired function of the original protein. In fact, modified peptides (i.e., peptides composed of an amino acid sequence in which one, two or several amino acid residues have been modified (i.e., substituted, deleted, added or inserted as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence selected from among SEQ ID NO: 1, 2, 3, 4, 16, 17, 30, 31, 34, 36, 37, 40, 41, 45, 49, 55, 57 and 61, wherein one, two or even more amino acids are added, inserted, deleted and/or substituted.

Those skills in the art recognize that individual substitutions to an amino acid sequence which alters a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the modified peptide retains the CTL inducibility of the original peptide. Furthermore, modified peptides should not exclude CTL inducible peptides of polymorphic variants, interspecies homologues, and alleles of WDRPUH.

To retain the requisite CTL inducibility one can modify (insert, delete, add and/or substitute) a small number (for example, 1, 2 or several) or a small percentage of the amino acids. Herein, the term "several" means 5 or fewer amino acids, for example, 4, 3 or fewer. The percentage of amino acids to be modified is preferably 20% or less, more preferably 15% or less, even more preferably 10% or less, or 1 to 5%.

Moreover, amino acid residues may be substituted, inserted, deleted and/or added in the peptides to yield a modified peptide having improved binding affinity. When used in the context of immunotherapy, peptides of the present invention should be presented on the surface of a cell or exosome, preferably as a complex with an HLA antigen. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. For example, it may be desirable to substitute the second amino acid from the N-terminus substituted with phenylalanine, tyrosine, methionine, or tryptophan, and/or the amino acid at the C-terminus with phenylalanine, leucine, isoleucine, tryptophan, or methionine in order to increase the HLA-A24 binding. Thus, peptides having the amino acid sequences selected from the group consisting of SEQ ID NOs: 1, 2, 3, 4, 16 and 17 wherein the second amino acid from the N-terminus of the amino acid sequence of the SEQ ID NOs is substituted with phenylalanine, tyrosine, methionine, or tryptophan, and peptides, and/or wherein the C-terminus of the amino acid sequence of the SEQ ID NOs is substituted with phenylalanine, leucine, isoleucine, tryptophan, or methionine are encompassed by the present invention. On the other hand, peptides possessing high HLA-A2 binding affinity have their second amino acid from the N-terminus substituted with leucine or methionine, and the amino acid at the C-terminus is substituted with valine or leucine. Thus, peptides having the amino acid sequences of SEQ ID NOs: 30, 31, 34, 36, 37, 40, 41, 45, 49, 55, 57 and 61 wherein the second amino acid from the N-terminus is substituted with leucine or methionine, and/or wherein the C-terminus is substituted with valine or leucine are encompassed by the present invention. Substitutions can be introduced not only at the terminal amino acids but also at the position of potential T cell receptor (TCR) recognition of peptides. Several studies have demonstrated that a peptide with amino acid substitutions can be equal to or better than the original, for example CAP1, p53$_{(264-272)}$, Her-2/neu$_{(366-377)}$ or gp100$_{(209-217)}$ (Zaremba et al. Cancer Res. 57, 4570-4577, 1997, T. K. Hoffmann et al. J. Immunol. (2002) February 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the described peptides. Such modified peptides having high HLA antigen binding affinity and retaining CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTLs against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependence on HLA class II restricted T(H) response) can be used. For example, the target cells can be radio-labeled with $^{51}$Cr and such, and cytotoxic activity can be calculated from radioactivity released from the target cells. Alternatively, CTL inducibility can be assessed by measuring IFN-gamma produced and released by CTLs in the presence of APCs that carry immobilized peptides, and visualizing the inhibition zone on the media using anti-IFN-gamma monoclonal antibodies.

As a result of examining the CTL inducibility of the peptides as described above, the nonapeptides or decapeptides having an amino acid sequence selected from among SEQ ID NOs: 1, 2, 3, 4, 16, 17, 30, 31, 34, 36, 37, 40, 41, 45, 49, 55, 57 and 61 were found to exhibit particularly high CTL inducibility as well as high binding affinity to an HLA antigen. Thus, these peptides are exemplified as preferred embodiments of the present invention.

Furthermore, the result of homology analysis showed that these peptides do not have significant homology with peptides derived from any other known human gene products. This means that the possibility of unknown or undesired immune responses arising due to the use of the present peptides in immunotherapy is low. Therefore, also from this aspect, these peptides are preferable for eliciting immunity in cancer patients against WDRPUH. Thus, particularly preferred peptides of the present invention include those having the amino acid sequence selected from among SEQ ID NOs: 1, 2, 3, 4, 16, 17, 30, 31, 34, 36, 37, 40, 41, 45, 49, 55, 57 and 61.

In addition the above-described modifications, the peptides of the present invention can also be linked to other peptides, so long as the resulting peptide retains the requisite CTL inducibility of the original peptide. Examples of suitable peptides include, but are not limited to: the peptides of the present invention or CTL inducible peptides derived from other TAAs. Linkers to be placed between the peptides are well known in the art and include, but are not limited to, for example, AAY (P. M. Daftarian et al., J Trans Med 2007, 5:26), AAA, NKRK (R. P. M. Sutmuller et al., J. Immunol. 2000, 165: 7308-7315) and K (S. Ota et al., Can Res. 62, 1471-1476, K. S. Kawamura et al., J. Immunol. 2002, 168: 5709-5715).

Furthermore, the peptides of the present invention can also be linked to other substances, so long as the resulting peptide retains the requisite CTL inducibility of the original peptide. Examples of suitable substances include, but are not limited to: peptides, lipids, sugar and sugar chains, acetyl groups, natural and synthetic polymers, etc, provided the modifications do not destroy the biological activity of the original peptide. The peptides can contain modifications such as glycosylation, side chain oxidation, or phosphorylation, etc, provided the modifications do not destroy the biological activity of the original peptide. These kinds of modifications can be performed to confer additional functions (e.g., targeting function, and delivery function) or to stabilize the polypeptide. For example, to increase the in vivo stability of a polypeptide, it is known in the art to introduce D-amino acids, amino acid mimetics or unnatural amino acids; this concept can also be adapted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

As noted above, it is possible to screen or select peptides that are modified by substitution, insertion, deletion and/or addition of one, two or several amino acid residues, but still having the same or higher activity as compared to the original peptide. Thus, the present invention also provides a method for screening or selecting a modified peptide having the same or higher activity as compared to the original peptide. For example, such method may be composed of the steps as follows:

a: modifying at least one amino acid residue in a peptide of the present invention by substitution, deletion, insertion and/or addition;

b: determining the activity of the modified peptide; and c: selecting the peptide which was determined to have the same or higher activity as compared to the original peptide.

Herein, the activity to be determined in step b may be the MHC binding activity, APC or CTL inducibility, and/or cytotoxic activity.

Herein, the peptides of the present invention can also be described as "WDRPUH peptide(s)" or "WDRPUH polypeptide(s)".

III. PREPARATION OF WDRPUH PEPTIDES

The peptides of the invention can be prepared using well known techniques. For example, the peptides can be prepared synthetically, using recombinant DNA technology or chemical synthesis. The peptides of the invention can be synthesized individually or as longer polypeptides composed of two or more peptides. The peptides can then be isolated i.e., purified or isolated so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted for the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adapting an in vitro translation system.

IV. POLYNUCLEOTIDES

The present invention also provides a polynucleotide which encodes any of the aforementioned peptides of the present invention. These include polynucleotides derived from the natural occurring WDRPUH gene (GenBank Accession No. NM_145697 (SEQ ID NO: 34)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J. 1984, 3: 801-5.

V. EXOSOMES

The present invention further provides intracellular vesicles called exosomes, which present complexes formed between the peptides of this invention and HLA antigens on their surface. Exosomes can be prepared, for example by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

The type of HLA antigens contained in the complexes must match that of the subject requiring treatment and/or prevention. For example, in the Japanese population, HLA-A24 and HLA-A2, particularly HLA-A2402 and HLA-A0201 or HLA-A0206 is prevalent and therefore would be appropriate for treatment of Japanese patient. The use of the A24 type or the A2 type that is highly expressed among the Japanese and Caucasian is favorable for obtaining effective results, and subtypes such as A2402, A0201 or A0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion, deletion and/or addition of 1, 2, or several amino acids can be performed based on the amino acid sequence of the naturally occurring WDRPUH partial peptide.

When using the A24 type HLA antigen for the exosome of the present invention, the peptides having the sequences selected from among SEQ ID NOs: 1, 2, 3, 4, 16, and 17 find use. Alternatively, when using the A2 type HLA antigen for the exosome of the present invention, the peptides having a sequence of any one of SEQ ID NOs: 30, 31, 34, 36, 37, 40, 41, 45, 49, 55, 57 and 61 find use.

VI. ANTIGEN-PRESENTING CELLS (APCs)

The present invention also provides isolated APCs that present complexes formed between HLA antigens and the peptides of this invention on its surface. The APCs can be derived from patients who are subject to treatment and/or prevention, and can be administered as vaccines by themselves or in combination with other drugs including the peptides of this invention, exosomes, or CTLs.

The APCs are not limited to a particular kind of cells and include DCs, Langerhans cells, macrophages, B cells, and activated T cells, which are known to present proteinaceous antigens on their cell surface so as to be recognized by lymphocytes. Since DC is a representative APC having the strongest CTL inducing action among APCs, DCs find use as the APCs of the present invention.

For example, an APC of the present invention can be obtained by inducing DCs from peripheral blood monocytes and then contacting (stimulating) them with the peptides of this invention in vitro, ex vivo or in vivo. The phrase "inducing APCs" includes contacting (stimulating) a cell with the peptides of this invention, or nucleotides encoding the peptides of this invention to present complexes formed between HLA antigens and the peptides of this invention on the cell's surface. When the peptides of this invention are administered to a subject, APCs that present the peptides of this invention are induced in the body of the subject. Therefore, the APCs of this invention can be obtained by collecting the APCs from a subject after administering a peptide of this invention to the subject. Alternatively, the APCs of this invention can be obtained by contacting APCs collected from a subject with the peptide of this invention.

The APCs of the present invention can be administered to a subject for inducing immune response against caner in the subject by themselves or in combination with other drugs including the peptides, exosomes or CTLs of this invention. For example, the ex vivo administration can include the steps of:

a: collecting APCs from a first subject;
b: contacting the APCs of step a with the peptide; and
c: administering the peptide-loaded APCs of step b to a second subject.

The first subject and the second subject can be the same individual, or may be different individuals. The APCs obtained by step b can be administered as a vaccine for treating and/or preventing cancer including hepatocellular carcinoma. In addition, the present invention provides a method or process for manufacturing a pharmaceutical composition inducing antigen-presenting cells, wherein the method contains the step of admixing or formulating the peptide of the present invention with a pharmaceutically acceptable carrier.

According to an aspect of the present invention, the APCs have a high level of CTL inducibility. In the term of "high level of CTL inducibility", the high level is relative to the level of that achieved by APCs contacted with no peptide or peptides which can not induce CTLs. Such APCs having a high level of CTL inducibility can be prepared by a method which includes the step of transferring genes containing the polynucleotides of this invention to APCs in vitro as well as by the method mentioned above. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed and presented by MHC Class I or Class II through a presentation pathway.

VII. CYTOTOXIC T LYMPHOCYTES (CTLs)

A CTL induced against any of the peptides of the present invention strengthens the immune response targeting cancer cells in vivo and thus can be used as vaccines, in a fashion similar to the peptides per se. Thus, the present invention also provides isolated CTLs that are specifically induced or activated by any of the present peptides.

Such CTLs can be obtained by (1) administering the peptides of the present invention to a subject, collecting CTLs from the subject; (2) contacting (stimulating) subject-derived APCs and CD8-positive cells, or peripheral blood mononuclear leukocytes in vitro with the peptides of the present invention and then isolating CTLs; (3) contacting CD8-positive cells or peripheral blood mononuclear leukocytes in vitro with the APCs or exosomes presenting a complex of an HLA antigen and a peptide of present invention on its surface and then isolating CTLs; or (4) introducing into a T cell, a gene encoding a T cell receptor (TCR) subunit polypeptide which binds to a peptide of this invention. The APCs or exosomes can be prepared by the methods described above, and the method of (4) is detailed below under the section of "VIII. T cell receptor (TCR)".

The CTLs of this invention, which have been induced by stimulation with APCs that present a peptide of this invention, can be derived from patients who are subject to treatment and/or prevention, and can be administered by themselves or in combination with other drugs including the peptides of this invention or exosomes for the purpose of regulating effects. The obtained CTLs act specifically against target cells presenting the peptides of this invention, for example, the same peptides used for induction. The target cells can be cells that endogenously express WDRPUH, for example, hepatocellular carcinoma, or cells that are transfected with the WDRPUH gene; and cells that present a peptide of this invention on the cell surface due to stimulation by the peptide can also serve as targets of activated CTL attack.

VIII. T CELL RECEPTOR (TCR)

The present invention also provides a composition containing nucleic acids encoding polypeptides that are capable of forming a subunit of a T cell receptor (TCR), and methods of using the same. The TCR subunits have the ability to form TCRs that confer specificity to T cells against tumor cells presenting the specific peptide of the present invention. By using known methods in the art, the nucleic acids of alpha- and beta-chains as the TCR subunits of the CTL induced with one or more peptides of this invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 65) and 3-TRa-C primers (5'-tcagctggaccacagccgcagcgt-3') specific to TCR alpha chain C region (SEQ ID NO: 66), 3-TRb-C1 primers (5'-tcagaaatcctttctcttgac-3') specific to TCR beta chain C1 region (SEQ ID NO: 67) or 3-TRbeta-C2 primers (5'-ctagcctctggaatcctttctctt-3') specific to TCR beta chain C2 region (SEQ ID NO: 68) as 3' side primers, but not limited. The derivative TCR can bind target cells displaying the WDRPUH peptide with high avidity, and optionally mediate efficient killing of target cells presenting the WDRPUH peptide in vivo and in vitro.

The nucleic acids encoding the TCR subunits can be incorporated into suitable vectors e.g. retroviral vectors. These vectors are well known in the art. The nucleic acids or the vectors containing them usefully can be transferred into a T cell, for example, a T cell from a patient. Advantageously, the invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR on the surface of the T cell. A specific recognition of the above complex may be confirmed by any known methods, and preferred methods include, for example, tetramer analysis using HLA molecule and peptide of the invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay. Also, the present invention provides CTLs which are prepared by transduction with the nucleic acids encoding the TCR subunits polypeptides that bind to the WDRPUH peptide of, e.g., SEQ ID NOs: 1, 2, 3, 4, 16 and 17 in the context of HLA-A2, and also the peptides of SEQ ID NOs: 30, 31, 34, 36, 37, 40, 41, 45, 49, 55, 57 and 61 in the context of HLA-A24. The transduced CTLs are capable of homing to cancer cells in vivo, and can be expanded by well known culturing methods in vitro (e.g., Kawakami et al., J. Immunol., 142, 3452-3461 (1989)). The CTLs of the invention can be used to form an immunogenic composition useful in the treatment or prophylaxis of cancer in a patient in need of therapy or protection (WO2006/031221).

Prevention and prophylaxis include any activity which reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

Treatment and/or prophylaxis of cancer or, and/or prevention of postoperative recurrence thereof includes any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effective treatment and/or prophylaxis, and such reduction or improvement of symptoms include 10%, 20%, 30% or more reduction, or sustaining a stable disease state.

IX. PHARMACEUTICAL AGENTS OR COMPOSITIONS

Since WDRPUH expression is specifically elevated (upregulated) in hepatocellular carcinoma as compared with normal tissue (Silva et al., Neoplasia 2005 April; 7(4):348-55), the peptides or polynucleotides of the present invention can be used for the treatment and/or the prophylaxis of cancer or tumor, and/or prevention of post-operative recurrence thereof. Thus, the present invention provides a pharmaceutical agent or composition for the treatment and/or the prophylaxis of cancer or tumor, and/or prevention of postoperative recurrence thereof, which includes one or more of the peptides, or polynucleotides of this invention as an active ingredient. Alternatively, the present peptides can be expressed on the surface of any of the foregoing exosomes or cells, such as APCs for the use as pharmaceutical agents or compositions. In addition, the aforementioned CTLs which target any of the peptides of the invention can also be used as the active ingredient of the present pharmaceutical agents or compositions.

In another embodiment, the present invention also provide the use of an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a CTL of the present invention
in manufacturing a pharmaceutical composition or agent for treating or preventing cancer or tumor.

Alternatively, the present invention further provides an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a CTL of the present invention
for use in treating or preventing cancer or tumor.

Alternatively, the present invention further provides a method or process for manufacturing a pharmaceutical composition or agent for treating or preventing cancer or tumor, wherein the method or process includes the step of formulating a pharmaceutically or physiologically acceptable carrier with an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a CTL of the present invention
as active ingredients.

In another embodiment, the present invention also provides a method or process for manufacturing a pharmaceutical composition or agent for treating or preventing cancer or tumor, wherein the method or process includes the step of admixing an active ingredient with a pharmaceutically or physiologically acceptable carrier, wherein the active ingredient is selected from among:
(a) a peptide of the present invention;
(b) a nucleic acid encoding such a peptide as disclosed herein in an expressible form;
(c) an APC or an exosome presenting a peptide of the present invention on its surface; and
(d) a CTL of the present invention.

Alternatively, the pharmaceutical composition or agent of the present invention may be used for either or both the prophylaxis of cancer or tumor and prevention of post-operative recurrence thereof.

The present pharmaceutical agents or compositions find use as a vaccine. In the context of the present invention, the phrase "vaccine" (also referred to as an immunogenic composition) refers to a substance that has the function to induce anti-tumor immunity upon inoculation into animals.

The pharmaceutical agents or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence selected from among SEQ ID NOs: 1, 2, 3, 4, 16, 17, 30, 31, 34, 36, 37, 40, 41, 45, 49, 55, 57 and 61 have been found to be HLA-A24 or HLA-A2 restricted epitope peptides or candidates, respectively, that can induce potent and specific immune response. Therefore, the present pharmaceutical agents which include any of these peptides having the amino acid sequences of SEQ ID NOs: 1, 2, 3, 4, 16, 17, 30, 31, 34, 36, 37, 40, 41, 45, 49, 55, 57 and 61 are particularly suited for the administration to subjects whose HLA antigen is HLA-A24 or HLA-A2. Especially, agents containing peptides having an amino acid sequence of SEQ ID NOs: 1, 2, 3, 4, 16 and 17 are suited for the administration to subjects of the HLA-A24 type, and those having an amino acid sequence of SEQ ID NOs: 30, 31, 34, 36, 37, 40, 41, 45, 49, 55, 57 and 61 are suited for the administration to subjects of the HLA-A2 type. The same applies to pharmaceutical agents and compositions which include polynucleotides encoding any of these peptides (i.e. the polynucleotides of this invention).

Cancers or tumors to be treated by the pharmaceutical agents or compositions of the present invention are not limited and include all kinds of cancers or tumors wherein WDRPUH is involved, for example, hepatocellular carcinoma.

The present pharmaceutical agents or compositions can contain in addition to the aforementioned active ingredients, other peptides which have the ability to induce CTLs against cancerous cells, other polynucleotides encoding the other peptides, other cells that present the other peptides, or such.

Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents or compositions of this invention can include other agents conventional in the art having regard to the type of formulation in question.

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents with a label. Suitable containers include bottles, vials, and test tubes. The containers can be formed from a variety of materials, such as glass or plastic. The label on the container should indicate the agent or composition is used for treating or preventing one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of this invention can be administered directly as a pharmaceutical agent or composition, or if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared as a combination composed of two or more of the peptides of the present invention, to induce CTLs in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA antigens on APCs, then CTLs that specifically react toward the complex formed between the displayed peptide and the HLA antigen are induced. Alternatively, APCs that present any of the peptides of this invention on their cell surface, which may be obtained by stimulating APCs (e.g., DCs) derived from a subject with the peptides of this invention may be administered to the subject, and as a result, CTLs are induced in the subject and aggressiveness towards the cancer cells can be increased.

The pharmaceutical agents or composition for the treatment and/or prevention of cancer or tumor, which include a peptide of this invention as the active ingredient, can also include an adjuvant known to effectively establish cellular immunity. Alternatively, the pharmaceutical agents or compositions can be administered with other active ingredients or administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include aluminum phosphate, aluminum hydroxide, alum, cholera toxin, *salmonella* toxin, and such, but are not limited thereto.

Furthermore, liposome formulations, granular formulations in which the peptide is bound to few-micrometers diameter beads, and formulations in which a lipid is bound to the peptide may be conveniently used.

In some embodiments, the pharmaceutical agents or compositions of the present invention may further include a component which primes CTLs. Lipids have been identified as agents capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming CTLs responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every few days to once every few months. One skilled in the art can appropriately select the suitable dose.

X. METHODS USING THE PEPTIDES, EXOSOMES, APCs AND CTLs

The peptides and polynucleotides of the present invention can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can be also be used for inducing APCs as discussed below.

(1) Method of Inducing Antigen-Presenting Cells (APCs)

The present invention provides methods of inducing APCs with high CTL inducibility using the peptides or polynucleotides of this invention.

The methods of the present invention contain the step of contacting APCs with the peptides of this invention in vitro, ex vivo or in vivo. For example, the method contacting APCs with the peptides ex vivo can include the steps of:

a: collecting APCs from a subject; and b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of this invention.

Alternatively, APCs may be induced by administering a peptide of the present invention to a subject to contact the peptide with APCs in vivo, and consequently, induce APCs with high CTL inducibility in the body of the subject. Thus, the present invention also contemplates administering the peptides of this invention to a subject for inducing APCs. As another method, a polynucleotide of this invention may be administered to a subject in an expressible form to express a peptide of this invention and contact the peptide with APCs in vivo. Similarly to the administration of a peptide of the present invention, APCs with high CTL inducibility are induced in the body of the subject. Thus, the present invention also contemplates administering the polynucleotides of this invention to a subject for inducing APCs. For the explanation on the phrase of "expressible form", see section "IX. Pharmaceutical agents (2) Pharmaceutical agents containing polynucleotides as the active ingredient".

Furthermore, the present invention also contemplates introducing a polypeptide of this invention into an APC to induce APC with CTL inducibility. For example, the method may include the steps of:

a: collecting an APC from a subject; and b: introducing a polynucleotide encoding a peptide of this invention into the collected APC.

The step b can be performed as described above in section "VI. Antigen-presenting cells".

(2) Method of Inducing CTLs

Furthermore, the present invention provides methods for inducing CTLs using the peptides, polynucleotides, or exosomes or APCs of this invention.

Upon the administration of the peptides, the polynucleotides, APCs, or exosomes of this invention to a subject, CTLs are induced in the body of the subject to strengthen the immune response targeting cancer cells. Thus, it is another object of the present invention to provide a method for inducing CTLs, which method may include the step of administering the peptides, the polynucleotides, the APCs or exosomes of this invention to a subject.

Alternatively, CTLs can be also induced ex vivo, and after the induction, the activated CTLs may be returned to the subject. For example, the method may include the steps of:

a: collecting APCs from a subject;

b: contacting the APCs of step a with a peptide of the present invention; and c: co-culturing the APCs of step b with CD8-positive cells.

The APCs to be co-cultured with the CD8-positive cells in above step c can also be prepared by transferring a polynucleotide encoding the peptide of this invention into APCs as described above in section "VI. Antigen-presenting cells"; but are not limited thereto and any APCs which effectively presents, on its surface, a complex of an HLA antigen and a peptide of this invention may be used for the present method.

In place of such APCs, exosomes that present on their surface a complex of an HLA antigen and a peptide of this invention may be also used. Namely, the present inventive method for inducing CTLs may include the step of co-culturing exosomes presenting on its surface a complex of an HLA antigen and a peptide of this invention. Such exosomes may be prepared by the methods described above in section "V. Exosomes".

Furthermore, CTLs can be induced by introducing a polynucleotide encoding a TCR subunit binding to a peptide of this invention into CD8-positive cells. Such transduction may be performed as described above in section "VIII. T cell receptor (TCR)".

(3) Method of Inducing Immune Response

The present invention further provides methods for inducing an immune response against cancer in a subject. The methods include the administration of a vaccine of the present invention, which contains:

(a) one or more peptides of the present invention, or an immunologically active fragment thereof;

(b) one or more polynucleotides encoding the peptides or the immunologically active fragment of (a);

(c) one or more isolated CTLs of the present invention; or (d) one or more isolated antigen-presenting cells of the present invention.

In the present invention, cancer overexpressing WDRPUH can be treated with these active ingredients. Accordingly, prior to the administration of the vaccines or pharmaceutical compositions comprising the active ingredients, it is preferable to confirm whether the expression level of WDRPUH in the cancer cells or tissues to be treated is enhanced compared with normal cells of the same organ. Thus, in one embodiment, the present invention provides a method for treating cancer expressing WDRPUH, which method may include the steps of:

i) determining the expression level of WDRPUH in cancer cells or tissue obtained from a subject with the cancer to be treated;

ii) comparing the expression level of WDRPUH with normal control; and iii) administrating at least one component selected from the group consisting of (a) to (d) described above to a subject with cancer overexpressing WDRPUH compared with normal control.

Alternatively, the present invention also provides a vaccine or pharmaceutical composition comprising at least one component selected from the group consisting of (a) to (d) described above, for use in administrating to a subject having cancer overexpressing WDRPUH. In other words, the present invention further provides a method for identifying a subject to be treated with the WDRPUH polypeptide of the present invention, which method may include the step of determining an expression level of WDRPUH in subject-derived cancer cells or tissue, wherein an increase of the level compared to a normal control level of the gene indicates that the subject has cancer which may be treated with the WDRPUH polypeptide of the present invention. The method of treating cancer of the present invention will be described in more detail below.

A subject to be treated by the present method is preferably a mammal. Exemplary mammals include, but are not limited to, e.g., human, non-human primate, mouse, rat, dog, cat, horse, and cow.

According to the present invention, the expression level of WDRPUH in the cancer cells or tissues obtained from a subject is determined. The expression level can be determined at the transcription (nucleic acid) product level, using methods known in the art. For example, the mRNA of WDRPUH may be quantified using probes by hybridization methods (e.g., Northern hybridization). The detection may be carried out on a chip or an array. The use of an array is preferable for detecting the expression level of WDRPUH. Those skilled in the art can prepare such probes utilizing the sequence information of WDRPUH. For example, the cDNA of WDRPUH may be used as the probes. If necessary, the probe may be labeled with a suitable label, such as dyes, fluorescent substances and isotopes, and the expression level of the gene may be detected as the intensity of the hybridized labels. Furthermore, the transcription product of WDRPUH (SEQ ID NO: 63) may be quantified using primers by amplification-based detection methods (e.g., RT-PCR). Such primers can also be prepared based on the available sequence information of the gene.

Specifically, a probe or primer used for the present method hybridizes under stringent, moderately stringent, or low stringent conditions to the mRNA of WDRPUH. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of WDRPUH protein (SEQ ID NO: 64) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment or modified antibody retains the binding ability to WDRPUH protein. Methods to prepare these kinds of antibodies for the detection of proteins are well known in the art, and any method may be employed in the present invention to prepare such antibodies and equivalents thereof. As another method to detect the expression level of WDRPUH gene based on its translation product, the intensity of staining may be observed via immunohistochemical analysis using an antibody against WDRPUH protein. Namely, the observation of strong staining indicates increased presence of the protein and, at the same time, high expression level of WDRPUH gene.

The expression level of target gene including WDRPUH gene in cancer cells can be considered to be increased if it increases from the control level of the corresponding the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time with the cancer cells by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of WDRPUH gene in samples from subjects whose disease states are known. Furthermore, the control level can be a database of expression patterns from previously tested cells.

Moreover, according to an aspect of the present invention, the expression level of WDRPUH gene in a biological sample may be compared to multiple control levels, which control levels are determined from multiple reference samples. It is preferred to use a control level determined from a reference sample derived from a tissue type similar to that of the subject-derived biological sample. Moreover, it is preferred, to use the standard value of the expression levels of WDRPUH gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level".

When the expression level of WDRPUH gene is increased as compared to the normal control level or is similar to the cancerous control level, the subject may be diagnosed with cancer to be treated.

The present invention also provides a kit for determining a subject suffering from cancer which can be treated with the WDRPUH polypeptide of the present invention, which may also be useful in assessing and/or monitoring the efficacy of a cancer immunotherapy. Preferably, the cancer is hepatocellular carcinoma. More particularly, the kit preferably includes at least one reagent for detecting the expression of the WDRPUH gene in a subject-derived cancer cell, which reagent may be selected from the group of:

(a) a reagent for detecting mRNA of the WDRPUH gene;
(b) a reagent for detecting the WDRPUH protein; and
(c) a reagent for detecting the biological activity of the WDRPUH protein.

Suitable reagents for detecting mRNA of the WDRPUH gene include nucleic acids that specifically bind to or identify the WDRPUH mRNA, such as oligonucleotides which have a complementary sequence to a part of the WDRPUH mRNA. These kinds of oligonucleotides are exemplified by primers and probes that are specific to the WDRPUH mRNA. These kinds of oligonucleotides may be prepared based on methods well known in the art. If needed, the reagent for detecting the WDRPUH mRNA may be immobilized on a solid matrix. Moreover, more than one reagent for detecting the WDRPUH mRNA may be included in the kit.

On the other hand, suitable reagents for detecting the WDRPUH protein include antibodies to the WDRPUH protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment or modified antibody retains the binding ability to the WDRPUH protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of antibodies to their targets are well known in the art, and any labels and methods may be employed for the present invention. Moreover, more than one reagent for detecting the WDRPUH protein may be included in the kit.

The kit may contain more than one of the aforementioned reagents. For example, tissue samples obtained from subjects suffering from cancer or not may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

As an embodiment of the present invention, when the reagent is a probe against the WDRPUH mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of WDRPUH mRNA present in the sample. The detection sites may be configured in any suitably detectable shape and are typically in the shape of a bar or dot spanning the width of a test strip.

The kit of the present invention may further include a positive control sample or WDRPUH standard sample. The positive control sample of the present invention may be prepared by collecting WDRPUH positive samples and then those WDRPUH level are assayed. Alternatively, purified WDRPUH protein or polynucleotide may be added to cells non-expressing WDRPUH to form the positive sample or the WDRPUH standard. In the present invention, purified WDRPUH may be recombinant protein. The WDRPUH level of the positive control sample is, for example, more than the cut off value.

The following examples are presented to illustrate the present invention and to assist one of ordinary skill in making and using the same. The examples are not intended in any way to otherwise limit the scope of the invention.

Examples

Materials and Methods

Cell Lines

A24 lymphoblastoid cell line (A24LCL) was established by transformation with Epstein-bar virus into HLA-A24 positive human B lymphocyte. T2 (HLA-A2), COS7, African green monkey kidney cell line, were purchased from ATCC.

Candidate Selection of Peptides Derived from WDRPUH 9-mer and 10-mer peptides derived from WDRPUH that bind to HLA-A*2402 and HLA-A*0201 molecules were predicted using binding prediction software "BIMAS" (http://www-bimas.cit.nih.gov/molbio/hla_bind) (Parker et al. (J Immunol 1994, 152(1): 163-75), Kuzushima et al. (Blood 2001, 98(6): 1872-81)). These peptides were synthesized by Sigma (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive and HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown).

These peptide-pulsed DCs were then inactivated by Mitomycin C (MMC) (30 micro-g/ml for 30 min) or X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time following the same steps as described above. CTLs were tested against peptide-pulsed A24LCL or T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-Dwell of AIM-V Medium containing 5% AS. 50 micro-l/well of IL-2 were added to the medium 10 days later so as to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed A24LCL ($1 \times 10^4$/well) or T2 ($1 \times 10^4$/well) was prepared as stimulator cells. Cultured cells in 48 wells were used as responder cells. IFN-gamma ELISPOT assay and IFN-gamma ELISA assay were performed according to the manufacture's recommended procedure.

Plasmid Transfection

The cDNAs encoding the open reading frames of target genes, HLA-A24 and HLA-A*0201 were amplified by PCR. The PCR-amplified product of Target genes and HLA-A24 or HLA-A*0201 were cloned into pIRES vector (Clontech Laboratories, Inc., Cat. No. 631605). The plasmids were transfected into COS7, which is a target genes and HLA-A24-null cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results

Prediction of HLA-A24 and HLA-A2 Binding Peptides Derived from WDRPUH

Table 1 shows the HLA-A24 binding peptides of WDRPUH in order of highest binding affinity. A total of 25 peptides having potential HLA-A24 binding ability were selected and examined to determine the epitope peptides (Table 1) Table 2 shows the HLA-A2 binding 9mer and 10mer peptides of WDRPUH in order of highest binding affinity. A total of 37 peptides having potential HLA-A2 binding ability were selected and examined to determine the epitope peptides (Table 2).

TABLE 1

HLA-A24 binding peptides derived from WDRPUH predicted by BIMAS

| Peptide name | Start Position | Amino Acid sequence | Binding Score | SEQ ID NO. |
|---|---|---|---|---|
| WDRPUH-A24-9 mer | 40 | IYPLGCTVL | 300 | 1 |
| | 314 | IYRVSFTDF | 120 | 2 |
| | 509 | CYHPEEFQI | 60 | 3 |
| | 339 | VFPFGTAEL | 33 | 4 |
| | 318 | SFTDFKETL | 24 | 5 |
| | 400 | AFAPETGRL | 24 | 6 |
| | 118 | AFSPNDLYL | 24 | 7 |
| | 231 | KMNPRTKLL | 14.4 | 8 |
| | 257 | RCLKMGGLL | 12 | 9 |
| | 99 | KNRELLARL | 11.52 | 10 |
| | 527 | AYWEVFDGT | 10.08 | 11 |
| | 248 | KFSLGVSAI | 10 | 12 |
| WDRPUH-A24-10 mer | 280 | GYKPiKKIQL | 240 | 13 |
| | 77 | EYIAsGQVTF | 150 | 14 |
| | 509 | CYHPeEFQII | 86.4 | 15 |
| | 409 | MYVInNAHRI | 75 | 16 |
| | 40 | IYPLgCTVLi | 75 | 17 |
| | 220 | FYLGtTTGDI | 75 | 18 |
| | 21 | GFNGhVPTGL | 42 | 19 |
| | 531 | VFDGtVIREL | 30.8 | 20 |
| | 559 | HFVTgGNDHL | 30 | 21 |
| | 495 | RNQMiLANTL | 17.28 | 22 |
| | 339 | VFPFgTAELF | 15 | 23 |
| | 165 | IFSRcRDEMF | 10 | 24 |
| | 331 | HFDAvEDIVF | 10 | 25 |

Start position indicates the number of amino acid residue from the N-terminus of WDRPUH.
Binding score is derived from "BIMAS".

TABLE 2

HLA-A2 binding peptides derived from WDRPUH predicted by BIMAS

| Peptide name | Start Position | Amino Acid sequence | Binding Score | SEQ ID NO. |
|---|---|---|---|---|
| WDPRUH-A2-9 mer | 59 | FLQGHGNNV | 319.939 | 26 |
| | 499 | ILANTLFQC | 112.664 | 27 |
| | 553 | ITQEGVHFV | 85.173 | 28 |
| | 231 | KMNPRTKLL | 53.999 | 29 |
| | 39 | MIYPLGCTV | 52.025 | 30 |
| | 407 | RLMYVINNA | 42.278 | 31 |
| | 264 | LLVGSGAGL | 36.316 | 32 |
| | 193 | KIWPTECQT | 29.766 | 33 |
| | 288 | QLQGGITSI | 23.995 | 34 |
| | 116 | ALAFSPNDL | 21.362 | 35 |
| | 237 | KLLTDVGPA | 19.236 | 36 |
| | 543 | SLSGSINGM | 11.426 | 37 |
| WDPRUH-A2-10 mer | 94 | ILWDyKNREL | 247.167 | 38 |
| | 499 | ILANtLFQCV | 224.653 | 39 |
| | 570 | KVWDyNEGEV | 94.23 | 40 |
| | 263 | GLLVgSGAGL | 79.041 | 41 |
| | 155 | GLNVgNATNV | 69.552 | 42 |
| | 498 | MILAnTLFQC | 57.318 | 43 |
| | 305 | FLVGtEESHI | 47.991 | 44 |
| | 78 | YIASgQVTFM | 39.75 | 45 |
| | 610 | AILRwKYPYT | 31.277 | 46 |
| | 86 | FMGFkADIIL | 29.098 | 47 |
| | 325 | TLIAtCHFDA | 28.814 | 48 |
| | 10 | QVAEIELDAV | 28.121 | 49 |
| | 560 | FVTGgNDHLV | 27.995 | 50 |
| | 108 | SLHKgKIEAL | 24.075 | 51 |
| | 374 | NMTChGIDFM | 22.24 | 52 |
| | 221 | YLGTtTGDIL | 19.742 | 53 |
| | 231 | KMNPrTKLLT | 18.837 | 54 |
| | 411 | VINNaHRIGV | 16.258 | 55 |
| | 51 | AINTkEQNFL | 16.155 | 56 |
| | 287 | IQLQgGITSI | 15.303 | 57 |
| | 326 | LIATcHFDAV | 15.136 | 58 |
| | 437 | GEGEvRVWQI | 14.347 | 59 |
| | 338 | IVFPfGTAEL | 11.757 | 60 |
| | 265 | LVGSgAGLLV | 10.346 | 61 |
| | 117 | LAFSpNDLYL | 10.264 | 62 |

Start position indicates the number of amino acid residue from the N-terminus of WDRPUH.
Binding score is derived from "BIMAS".

CTL Induction with the Predicted Peptides from WDRPUH Restricted with HLA-A*2402 and Establishment for CTL Lines Stimulated with WDRPUH Derived Peptides CTLs for those peptides derived from WDRPUH were generated according to the protocols as described in "Materials and Methods". Peptide specific CTL activity was determined by IFN-gamma ELISPOT assay (FIG. 1a-f). It showed that #3 and #6 stimulated with WDRPUH-A24-9-40 (SEQ ID NO: 1) (a), #8 with WDRPUH-A24-9-314 (SEQ ID NO: 2) (b), #2 and #6 with WDRPUH-A24-9-509 (SEQ ID NO: 3) (c), #1, #2 and #5 with WDRPUH-A24-9-339 (SEQ ID NO: 4) (d), #2, #3, #4, #6, #7 and #8 with WDRPUH-A24-10-409 (SEQ ID NO: 16) (e) and #5, #6 and #8 with WDRPUH-A24-10-40 (SEQ ID NO: 17) (f) demonstrated potent IFN-gamma production as compared to the control wells.

Furthermore, the cells in the positive well numbers #6 stimulated with SEQ ID NO: 1, #8 with SEQ ID NO: 2, #2 with SEQ ID NO: 3, #5 with SEQ ID NO: 4, #4 with SEQ ID NO: 16 and #6 with SEQ ID NO: 17 were expanded and established as CTL lines. CTL activity of these CTL lines was determined by IFN-gamma ELISA assay (FIG. 2a-f). All CTL lines demonstrated potent IFN-gamma production against the target cells pulsed with corresponding peptides as compared to target cells without peptide pulse. On the other hand, no CTL lines could be established by stimulation with other peptides shown in Table 1, despite the fact that the peptides were predicted to have a binding activity with HLA-A*2402 (data not shown). As a result, 6 peptides derived from WDRPUH were screened as peptides that can induce potent CTL lines.

Specific CTL Activity Against Target Cells Exogenously Expressing WDRPUH and HLA-A*2402

The established CTL lines raised against the peptides of the present invention were examined for their ability to recognize target cells that endogenously express WDRPUH and HLA-A*2402 molecule. Specific CTL activity against COS7 cells transfected with both the full length of WDRPUH and HLA-A*2402 molecule genes (a specific model for the target cells that exogenously express WDRPUH and HLA-A*2402 gene) was tested using the CTL lines raised by corresponding peptides as the effecter cells. COS7 cells transfected with either the full length of WDRPUH or HLA-A* 2402 gene were prepared as control. In FIG. 3, the CTLs stimulated with SEQ ID NO: 2 showed potent CTL activity against COS7 cells expressing both WDRPUH and HLA-A*2402. In contrast, no significant specific CTL activity was detected against the controls. Thus, these data clearly demonstrate that WDRPUH-A24-9-314 (SEQ ID NO: 2) was naturally processed and presented on the target cell's surface with HLA-A*2402 molecule and was recognized by CTLs. These results indicated that this peptide derived from WDRPUH may be applicable as cancer vaccines for patients with WDRPUH expressing tumors.

CTL Induction with the Predicted Peptides from WDRPUH Restricted with HLA-A*0201

CTLs recognizing peptides derived from WDRPUH were generated according to the protocols as described in "Materials and Methods". Peptide specific CTL activity was determined by IFN-gamma ELISPOT assay (FIG. 4a-l). The well numbers #2 and #7 stimulated with WDRPUH-A2-9-39 (SEQ ID NO: 30) (a), #2 with WDRPUH-A2-9-407 (SEQ ID NO: 31) (b), #3 with WDRPUH-A2-9-288 (SEQ ID NO: 34) (c), #6 with WDRPUH-A2-9-237 (SEQ ID NO: 36) (d), #4 with WDRPUH-A2-9-543 (SEQ ID NO: 37) (e), #4 with WDRPUH-A2-10-570 (SEQ ID NO: 40) (f), #2 and #8 with WDRPUH-A2-10-263 (SEQ ID NO: 41) (g), #5 with WDRPUH-A2-10-78 (SEQ ID NO: 45) (h), #2 with WDRPUH-A2-10-10 (SEQ ID NO: 49) (i), #6 with WDRPUH-A2-10-411 (SEQ ID NO: 55) (j), #7 with WDRPUH-A2-10-287 (SEQ ID NO: 57) (k) and #6 with WDRPUH-A2-10-265 (SEQ ID NO: 61) (l) demonstrated potent IFN-gamma production as compared to the control wells. On the other hand, no potent IFN-gamma production could be detected by stimulation with other peptides shown in Table 2, despite the fact that these peptides were predicted to have a binding activity with HLA-A*0201 (data not shown).

Establishment of CTL Lines and Clones Against WDRPUH Specific Peptides

The cells that showed peptide specific CTL activity by IFN-gamma ELISPOT assay in the well numbers #7 stimulated with SEQ ID NO: 30 and #3 with SEQ ID NO: 34 were expanded and established as CTL lines. CTL activity of these CTL lines was determined by IFN-gamma ELISA assay (FIGS. 5a and b). Both CTL lines demonstrated potent IFN-gamma production against the target cells pulsed with corresponding peptides as compared to the target cells without peptide pulse. Furthermore, CTL clones were established by limiting dilution from the CTL lines, and IFN-gamma production from the CTL clones against target cells pulsed with the corresponding peptides was determined by IFN-gamma ELISA assay. Potent IFN-gamma productions from CTL clones stimulated with SEQ ID NO: 30 and SEQ ID NO: 34 are demonstrated in FIGS. 5c and d.

Specific CTL Activity Against Target Cells Exogenously Expressing WDRPUH and HLA-A*0201

The established CTL clones raised against the peptides of present invention were examined for their ability to recognize target cells that endogenously express WDRPUH and HLA-A*0201 molecule. Specific CTL activity against COS7 cells transfected with both the full length of WDRPUH and HLA-A*0201 molecule genes (a specific model for the target cells that endogenously express WDRPUH and HLA-A*0201 gene) was tested using the CTL lines raised by corresponding peptides as the effector cells. COS7 cells transfected with either the full length of WDRPUH or HLA-A*0201 genes were prepared as controls. In FIG. 5e, the CTLs stimulated with SEQ ID NO: 34 showed potent CTL activity against COS7 cells expressing both WDRPUH and HLA-A*0201. In contrast, no significant specific CTL activity was detected against the controls. These data clearly demonstrate that the peptides of WDRPUH-A02-9-288 (SEQ ID NO: 34) were endogenously processed and presented on the target cell's surface with HLA-A*0201 molecule and were recognized by the CTLs. These results indicated that WDRPUH-A02-9-288 (SEQ ID NO: 34) may be applicable as cancer vaccines for patients with WDRPUH expressing tumors.

Homology Analysis of Antigen Peptides

The CTLs stimulated with

| | |
|---|---|
| WDRPUH-A24-9-40, | (SEQ ID NO: 1) |
| WDRPUH-A24-9-314, | (SEQ ID NO: 2) |
| WDRPUH-A24-9-509, | (SEQ ID NO: 3) |
| WDRPUH-A24-9-339, | (SEQ ID NO: 4) |
| WDRPUH-A24-10-409, | (SEQ ID NO: 16) |
| WDRPUH-A24-10-40, | (SEQ ID NO: 17) |
| WDRPUH-A02-9-39, | (SEQ ID NO: 30) |
| WDRPUH-A02-9-407, | (SEQ ID NO: 31) |
| WDRPUH-A02-9-288, | (SEQ ID NO: 34) |
| WDRPUH-A02-9-237, | (SEQ ID NO: 36) |
| WDRPUH-A02-9-543, | (SEQ ID NO: 37) |
| WDRPUH-A02-10-570, | (SEQ ID NO: 40) |
| WDRPUH-A02-10-263, | (SEQ ID NO: 41) |
| WDRPUH-A02-10-78, | (SEQ ID NO: 45) |
| WDRPUH-A02-10-10, | (SEQ ID NO: 49) |
| WDRPUH-A02-10-411, | (SEQ ID NO: 55) |
| WDRPUH-A02-10-287 and | (SEQ ID NO: 57) |
| WDRPUH-A02-10-265 | (SEQ ID NO: 61) | showed significant and specific CTL activity. This result may be due to the fact that these peptide sequences are homologous to peptides derived from other molecules that are known to sensitize the human immune system.

To exclude this possibility, homology analyses were performed for these peptide sequences using as queries the BLAST algorithm (http://www.ncbi.nlm.nih.gov/blast/blast.cgi) which revealed no sequence with significant homology. The results of homology analyses indicate that the sequences of

| | |
|---|---|
| WDRPUH-A24-9-40, | (SEQ ID NO: 1) |
| WDRPUH-A24-9-314, | (SEQ ID NO: 2) |
| WDRPUH-A24-9-509, | (SEQ ID NO: 3) |
| WDRPUH-A24-9-339, | (SEQ ID NO: 4) |
| WDRPUH-A24-10-409, | (SEQ ID NO: 16) |
| WDRPUH-A24-10-40, | (SEQ ID NO: 17) |
| WDRPUH-A02-9-39, | (SEQ ID NO: 30) |
| WDRPUH-A02-9-407, | (SEQ ID NO: 31) |
| WDRPUH-A02-9-288, | (SEQ ID NO: 34) |
| WDRPUH-A02-9-237, | (SEQ ID NO: 36) |
| WDRPUH-A02-9-543, | (SEQ ID NO: 37) |
| WDRPUH-A02-10-570, | (SEQ ID NO: 40) |
| WDRPUH-A02-10-263, | (SEQ ID NO: 41) |

-continued

| | |
|---|---|
| WDRPUH-A02-10-78, | (SEQ ID NO: 45) |
| WDRPUH-A02-10-10, | (SEQ ID NO: 49) |
| WDRPUH-A02-10-411, | (SEQ ID NO: 55) |
| WDRPUH-A02-10-287 and | (SEQ ID NO: 57) |
| WDRPUH-A02-10-265 | (SEQ ID NO: 61) | are unique and thus, there is little possibility, to our best knowledge, that these molecules raise unintended immunologic responses to some unrelated molecules.

In conclusion, novel HLA-A24 and A2 epitope peptides were identified and demonstrated to be applicable for cancer immunotherapy.

INDUSTRIAL APPLICABILITY

The present invention describes new TAAs, particularly those derived from WDRPUH which induce potent and specific anti-tumor immune responses and have applicability to cancer types such as hepatocellular carcinoma. Such TAAs warrants further development of the clinical application of peptide vaccination strategy in cancer.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. An isolated peptide of less than 15 amino acids selected from the group consisting of:
   (a) an isolated peptide, which comprises the amino acid sequence as shown in SEQ ID NO: 2; and
   (b) an isolated peptide, which comprises the amino acid sequence as shown in SEQ ID NO: 2 in which 1 or 2 amino acid(s) are substituted and/or added, wherein the added amino acid(s) are added to the N-terminus and/or the C-terminus.

2. The peptide of claim 1, wherein the peptide has one or both of the following characteristics:
   (a) the second amino acid from the N-terminus is selected from the group consisting of phenylalanine, tyrosine, methionine and tryptophan; and
   (b) the C-terminal amino acid is selected from the group consisting of phenylalanine, leucine, isoleucine, tryptophan and methionine.

3. The isolated peptide of claim 1, which binds to an HLA antigen.

4. The isolated peptide of claim 3, wherein the HLA antigen is HLA-A24.

5. The isolated peptide of claim 1, which is a nonapeptide or a decapeptide.

6. The isolated peptide of claim 1, which has CTL inducibility.

* * * * *